(12) United States Patent
Gao et al.

(10) Patent No.: US 9,217,155 B2
(45) Date of Patent: Dec. 22, 2015

(54) ISOLATION OF NOVEL AAV'S AND USES THEREOF

(75) Inventors: Guangping Gao, Westborough, MA (US); Phillip D. Zamore, Northborough, MA (US)

(73) Assignee: University of Massachusetts, Boston, MA (US)

(*) Notice: Subject to any disclaimer, the term of this patent is extended or adjusted under 35 U.S.C. 154(b) by 1054 days.

(21) Appl. No.: 12/686,097

(22) Filed: Jan. 12, 2010

(65) Prior Publication Data

US 2010/0186103 A1    Jul. 22, 2010

Related U.S. Application Data

(63) Continuation-in-part of application No. 12/473,917, filed on May 28, 2009, now abandoned.

(60) Provisional application No. 61/130,105, filed on May 28, 2008.

(51) Int. Cl.
*C12N 15/86* (2006.01)
*C12N 15/85* (2006.01)
*C12N 15/11* (2006.01)

(52) U.S. Cl.
CPC .......... *C12N 15/8509* (2013.01); *C12N 15/111* (2013.01); *C12N 15/86* (2013.01); *A01K 2217/058* (2013.01); *A01K 2227/105* (2013.01); *A01K 2267/0331* (2013.01); *C12N 2310/13* (2013.01); *C12N 2310/141* (2013.01); *C12N 2320/32* (2013.01); *C12N 2330/51* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,043,270 A | 8/1991 | Abrams et al. | |
| 5,478,745 A | 12/1995 | Samulski et al. | |
| 5,871,982 A | 2/1999 | Wilson et al. | |
| 6,001,650 A | 12/1999 | Colosi | |
| 6,083,716 A | 7/2000 | Wilson et al. | |
| 6,156,303 A | 12/2000 | Russell et al. | |
| 6,251,677 B1 | 6/2001 | Wilson et al. | |
| 6,365,394 B1 | 4/2002 | Gao et al. | |
| 6,475,469 B1 | 11/2002 | Montgomery | |
| 6,485,966 B2 | 11/2002 | Gao et al. | |
| 6,498,244 B1 | 12/2002 | Patel et al. | |
| 6,821,512 B1 | 11/2004 | Gao et al. | |
| 6,953,690 B1 | 10/2005 | Gao et al. | |
| 6,962,815 B2 | 11/2005 | Bartlett | |
| 7,022,519 B2 | 4/2006 | Gao et al. | |
| 7,198,951 B2 | 4/2007 | Gao et al. | |
| 7,235,393 B2 | 6/2007 | Gao et al. | |
| 7,238,526 B2 | 7/2007 | Wilson et al. | |
| 7,247,472 B2 | 7/2007 | Wilson et al. | |
| 7,282,199 B2 | 10/2007 | Gao et al. | |
| 7,344,872 B2 | 3/2008 | Gao et al. | |
| 7,427,396 B2 | 9/2008 | Arbetman et al. | |
| 7,456,015 B2 | 11/2008 | Bohn et al. | |
| 7,906,111 B2 | 3/2011 | Wilson et al. | |
| 8,222,221 B2 | 7/2012 | Corey et al. | |
| 8,734,809 B2 | 5/2014 | Gao et al. | |
| 2002/0019050 A1 | 2/2002 | Gao et al. | |
| 2003/0040101 A1 | 2/2003 | Wilson et al. | |
| 2003/0092161 A1 | 5/2003 | Gao et al. | |
| 2003/0096399 A1 | 5/2003 | Barber et al. | |
| 2003/0119191 A1 | 6/2003 | Gao et al. | |
| 2003/0138772 A1 | 7/2003 | Gao et al. | |
| 2003/0207259 A1* | 11/2003 | Gao et al. ............... | 435/5 |
| 2003/0228282 A1 | 12/2003 | Gao et al. | |
| 2004/0136963 A1 | 7/2004 | Wilson et al. | |
| 2004/0171807 A1 | 9/2004 | Gao et al. | |
| 2005/0014262 A1 | 1/2005 | Gao et al. | |
| 2005/0032219 A1 | 2/2005 | Aubourg et al. | |
| 2005/0037988 A1* | 2/2005 | Zamore et al. ............ | 514/44 |
| 2005/0069866 A1 | 3/2005 | Wilson et al. | |
| 2005/0137153 A1 | 6/2005 | McSwiggen et al. | |
| 2006/0018841 A1 | 1/2006 | Arbetman et al. | |
| 2006/0063174 A1 | 3/2006 | Turner et al. | |
| 2006/0292117 A1 | 12/2006 | Loiler et al. | |
| 2007/0004042 A1 | 1/2007 | Gao et al. | |
| 2007/0036760 A1 | 2/2007 | Wilson et al. | |
| 2007/0134203 A1 | 6/2007 | Gao et al. | |
| 2007/0292410 A1 | 12/2007 | Cashman et al. | |

(Continued)

FOREIGN PATENT DOCUMENTS

| | | | |
|---|---|---|---|
| WO | WO-03/042397 A2 | 5/2003 | |
| WO | WO-03/093460 A1 | 11/2003 | |

(Continued)

OTHER PUBLICATIONS

Grimm, D. et al., "Therapeutic application of RNAi: is mRNA targeting finally ready for prime time?", J. Clin. Invest., 2007, vol. 117: pp. 3633-3641.*
Genbank Submission; NCBI, Accession No. AAB95450; Rutledge et al.; Jan. 12, 1998.
Genbank Submission; NCBI, Accession No. AAS99264; Gao et al.; Jun. 24, 2004.
Genbank Submission; NCBI, Accession No. ABA71701; Schmidt et al.; May 10, 2006.
Genbank Submission; NCBI, Accession No. ACB55301; Vandenberghe et al.; Jul. 31, 2008.

(Continued)

*Primary Examiner* — Michael Burkhart
(74) *Attorney, Agent, or Firm* — Wolf, Greenfield & Sacks, P.C.

(57) ABSTRACT

The invention in some aspects relates to isolated nucleic acids, compositions, and kits useful for identifying adeno-associated viruses in cells. In some aspects, the invention provides kits and methods for producing somatic transgenic animal models using recombinant AAV (rAAV) to an animal having at least one transgene that expresses a small interfering nucleic acid or at least one binding site for a miRNA.

14 Claims, 14 Drawing Sheets

(56) References Cited

U.S. PATENT DOCUMENTS

| | | | |
|---|---|---|---|
| 2008/0075737 A1 | 3/2008 | Gao et al. |
| 2008/0075740 A1 | 3/2008 | Gao et al. |
| 2008/0090281 A1 | 4/2008 | Wilson et al. |
| 2008/0219954 A1 | 9/2008 | Gao et al. |
| 2008/0292595 A1 | 11/2008 | Arbetman et al. |
| 2009/0111766 A1 | 4/2009 | Atkinson et al. |
| 2009/0131355 A1 | 5/2009 | Bot et al. |
| 2009/0149409 A1 | 6/2009 | Bohn et al. |
| 2009/0197338 A1 | 8/2009 | Vandenberghe et al. |
| 2010/0028998 A1 | 2/2010 | Roelvink et al. |
| 2010/0104561 A1 | 4/2010 | Zhong et al. |
| 2010/0323001 A1 | 12/2010 | Pachuk |
| 2011/0172293 A1 | 7/2011 | Fish et al. |
| 2012/0137379 A1 | 5/2012 | Gao et al. |
| 2013/0101558 A1 | 4/2013 | Gao et al. |
| 2013/0195801 A1 | 8/2013 | Gao et al. |
| 2013/0281516 A1 | 10/2013 | Gao et al. |
| 2014/0142161 A1 | 5/2014 | Flotte et al. |
| 2014/0296486 A1 | 10/2014 | Gao et al. |
| 2014/0335054 A1 | 11/2014 | Gao et al. |

FOREIGN PATENT DOCUMENTS

| | | | |
|---|---|---|---|
| WO | WO-2005/033321 A2 | 4/2005 |
| WO | WO 2006/119432 A2 | 11/2006 |
| WO | WO 2007000668 A2 * | 1/2007 |
| WO | WO 2007/027775 A2 | 3/2007 |
| WO | WO 2007/127264 A2 | 11/2007 |
| WO | WO-2008/091703 A2 | 7/2008 |
| WO | WO 2008/147839 A1 | 12/2008 |
| WO | WO 2008/150897 A2 | 12/2008 |
| WO | WO 2009/109665 A1 | 9/2009 |
| WO | WO-2009/130208 A1 | 10/2009 |
| WO | WO 2009/146178 A1 | 12/2009 |
| WO | WO 2010/034314 A1 | 4/2010 |
| WO | WO 2010/071454 A1 | 6/2010 |
| WO | WO 2010/129021 A1 | 11/2010 |
| WO | WO 2010/138263 | 12/2010 |

OTHER PUBLICATIONS

Genbank Submission; NCBI, Accession No. NP_049542; Xiao et al.; Mar. 11, 2010.
Genbank Submission; NCBI, Accession No. YP_680426; Ruffing et al.; Nov. 19, 2010.
Genbank Submission; NCBI, Accession No. ACB55310; Vandenberghe et al.; Jul. 31, 2008.
Afione et al., In vivo model of adeno-associated virus vector persistence and rescue. J Virol. May 1996;70(5):3235-41.
Akache et al., The 37/67-kilodalton laminin receptor is a receptor for adeno-associated virus serotypes 8, 2, 3, and 9. J Virol. Oct. 2006;80(19):9831-6.
Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.
Bals et al., Transduction of well-differentiated airway epithelium by recombinant adeno-associated virus is limited by vector entry. J Virol. Jul. 1999;73(7):6085-8.
Barcia et al., Intraventricular and intracerebral delivery of anti-epileptic drugs in the kindling model. Neurotherapeutics. Apr. 2009;6(2):337-43.
Bernacki et al., Mucin gene expression during differentiation of human airway epithelia in vitro. Muc4 and muc5b are strongly induced. Am J Respir Cell Mol Biol. Apr. 1999;20(4):595-604.
Berns et al., Detection of adeno-associated virus (AAV)-specific nucleotide sequences in DNA isolated from latently infected Detroit 6 cells. Virology. Dec. 1975;68(2):556-60.
Beutler et al., AAV for pain: steps towards clinical translation. Gene Ther. Apr. 2009;16(4):461-9. Epub Mar. 5, 2009.
Bolstad et al., A comparison of normalization methods for high density oligonucleotide array data based on variance and bias. Bioinformatics. Jan. 22, 2003;19(2):185-93.

Brantly et al., Phase I trial of intramuscular injection of a recombinant adeno-associated virus serotype 2 alphal-antitrypsin (AAT) vector in AAT-deficient adults. Hum Gene Ther. Dec. 2006;17(12):1177-86.
Brown et al., A microRNA-regulated lentiviral vector mediates stable correction of hemophilia B mice. Blood. Dec. 15, 2007;110(13):4144-52. Epub Aug. 28, 2007.
Brown et al., Endogenous microRNA can be broadly exploited to regulate transgene expression according to tissue, lineage and differentiation state. Nat Biotechnol. Dec. 2007;25(12):1457-67. Epub Nov. 16, 2007.
Brown et al., Endogenous microRNA regulation suppresses transgene expression in hematopoietic lineages and enables stable gene transfer. Nat Med. May 2006;12(5):585-91. Epub Apr. 23, 2006.
Bukh, A critical role for the chimpanzee model in the study of hepatitis C. Hepatology. Jun. 2004;39(6):1469-75.
Calcedo et al., Worldwide epidemiology of neutralizing antibodies to adeno-associated viruses. J Infect Dis. Feb. 1, 2009;199(3):381-90.
Carter et al., Adeno-associated virus gene expression and regulation. CRC Handbook of parvoviruses. 1990:227-54.
Chadderton et al., Improved retinal function in a mouse model of dominant retinitis pigmentosa following AAV-delivered gene therapy. Mol Ther. Apr. 2009;17(4):593-9. Epub Jan. 27, 2009.
Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.
Chen et al., Efficient transduction of vascular endothelial cells with recombinant adeno-associated virus serotype 1 and 5 vectors. Hum Gene Ther. Feb. 2005;16(2):235-47.
Chirmule et al., Humoral immunity to adeno-associated virus type 2 vectors following administration to murine and nonhuman primate muscle. J Virol. MAr. 2000;74(5):2420-5.
Conlon et al., Efficient hepatic delivery and expression from a recombinant adeno-associated virus 8 pseudotyped alphal-antitrypsin vector. Mol Ther. Nov. 2005;12(5):867-75. Epub Aug. 8, 2005.
Conrad et al., Safety of single-dose administration of an adeno-associated virus (AAV)-CFTR vector in the primate lung. Gene Ther. Aug. 1996;3(8):658-68.
Crowe et al., A comparison in chimpanzees of the immunogenicity and efficacy of live attenuated respiratory syncytial virus (RSV) temperature-sensitive mutant vaccines and vaccinia virus recombinants that express the surface glycoproteins of RSV. Vaccine. Nov. 1, 1993;11(14):1395-404.
Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.
Ebert et al., MicroRNA sponges: competitive inhibitors of small RNAs in mammalian cells. Nat Methods. Sep. 2007;4(9):721-6. Epub Aug. 12, 2007.
Ehlert et al., Cellular toxicity following application of adeno-associated viral vector-mediated RNA interference in the nervous system. BMC Neurosci. Feb. 18, 2010;11(1):20.
Elmén et al., LNA-mediated microRNA silencing in non-human primates. Nature. Apr. 17, 2008;452(7189):896-9. Epub Mar. 26, 2008.
Engelhardt et al., Adenovirus-mediated transfer of the CFTR gene to lung of nonhuman primates: biological efficacy study. Hum Gene Ther. Dec. 1993;4(6):759-69.
Fire et al., Potent and specific genetic interference by double-stranded RNA in Caenorhabditis elegans. Nature. Feb. 19, 1998;391(6669):806-11.
Fischer et al., Successful transgene expression with serial doses of aerosolized rAAV2 vectors in rhesus macaques. Mol Ther. Dec. 2003;8(6):918-26.
Fisher et al., Transduction with recombinant adeno-associated virus for gene therapy is limited by leading-strand synthesis. J Virol. Jan. 1996;70(1):520-32.
Flotte et al., Phase I trial of intramuscular injection of a recombinant adeno-associated virus alpha 1-antitrypsin (rAAV2-Cb-hAAT) gene vector to AAT-deficient adults. Hum Gene Ther. Jan. 2004;15(1):93-128.
Flotte, Recombinant adeno-associated virus (AAV) gene therapy vectors for, cystic fibrosis (CF), alpha-1-antitrypsin deficiency (AAT) and fatty oxidation disorders (FAO). Umass Medical School.

(56) References Cited

OTHER PUBLICATIONS

Interdisciplinary Graduate Program. Last accessed at http://www.umassmed.edu/igp/faculty/flotte.cfm?start=0& on Aug. 27, 2009.
Foust et al., Intravascular AAV9 preferentially targets neonatal-neurons and adult-astrocytes in CNS. Nature Biotechnology, 27; 59-65 2009.
Fu et al., Evaluation of cellular immune responses in subjects chronically infected with HIV type 1. AIDS Res Hum Retroviruses. Jan. 2007;23(1):67-76.
Fu et al., Self-complementary adeno-associated virus serotype 2 vector: global distribution and broad dispersion of AAV-mediated transgene expression in mouse brain. Mol Ther. Dec. 2003;8(6):911-7.
Gao et al., Adeno-associated viruses undergo substantial evolution in primates during natural infections. Proc Natl Acad Sci U S A. May 13, 2003;100(10):6081-6. Epub Apr. 25, 2003.
Gao et al., Biology of AAV serotype vectors in liver-directed gene transfer to nonhuman primates. Mol Ther. Jan. 2006;13(1):77-87. Epub Oct. 10, 2005.
Gao et al., Clades of Adeno-associated viruses are widely disseminated in human tissues. J Virol. Jun. 2004;78(12):6381-8.
Gao et al., In situ synthesis of oligonucleotide microarrays. Biopolymers. Apr. 5, 2004;73(5):579-96.
Gao et al., Inadvertent gene transfer of co-packaged rep and cap sequences during the production of AAV vector and its potential impact on vector performance. Molecular Therapy. May 2008;16(Suppl. 1):S105-S106. Abstract 279.
Gao et al., New recombinant serotypes of AAV vectors. Curr Gene Ther. Jun. 2005;5(3):285-97.
Gao et al., Novel adeno-associated viruses from rhesus monkeys as vectors for human gene therapy. Proc Natl Acad Sci USA. Sep. 3, 2002;99(18):11854-9. Epub Aug. 21, 2002.
Gao et al., Purification of recombinant adeno-associated virus vectors by column chromatography and its performance in vivo. Hum Gene Ther. Oct. 10, 2000;11(15):2079-91.
Gao et al., RAAV-mediated targeting in adult mice and its potential in generating animal models of tissue-specific somatic transgenics or knock down. Molecular Therapy. May 2008;16(1):5118-5119. Abstract 316.
Grimm et al., Fatality in mice due to oversaturation of cellular microRNA/short hairpin RNA pathways. Nature. May 25, 2006;441(7092):537-41.
Gruenert et al., Culture and transformation of human airway epithelial cells. Am J Physiol. Mar. 1995;268(3 Pt 1):L347-60.
Hauswirth et al., Treatment of leber congenital amaurosis due to RPE65 mutations by ocular subretinal injection of adeno-associated virus gene vector: short-term results of a phase I trial. Hum Gene Ther. Oct. 2008;19(10):979-90.
Hernandez et al., Latent adeno-associated virus infection elicits humoral but not cell-mediated immune responses in a nonhuman primate model. J Virol. Oct. 1999;73(10):8549-58.
Hildinger et al., Hybrid vectors based on adeno-associated virus serotypes 2 and 5 for muscle-directed gene transfer. J Virol. Jul. 2001; 75(13):6199-203.
Kotin et al., Organization of adeno-associated virus DNA in latently infected Detroit 6 cells. Virology. Jun. 1989;170(2):460-7.
Kotin et al., Site-specific integration by adeno-associated virus. Proc Natl Acad Sci U S A. Mar. 1990;87(6):2211-5.
Kwiatkowski et al., Clinical, genetic, and pharmacogenetic applications of the Invader assay. Mol Diagn. Dec. 1999;4(4):353-64.
Lanford et al., Therapeutic silencing of microRNA-122 in primates with chronic hepatitis C virus infection. Science. Jan. 8, 2010;327(5962)198-201. Epub Dec. 3, 2009.
Li et al., Ex vivo transduction and transplantation of bone marrow cells for liver gene delivery of alpha1-antitrypsin. Mol Ther. Aug. 2010;18(8):1553-8. Epub Jun. 15, 2010.
Lin et al., Impact of preexisting vector immunity on the efficacy of adeno-associated virus-based HIV-1 Gag vaccines. Hum Gene Ther. Jul. 2008;19(7):663-9.
Liu et al., Biological Differences in rAAV Transduction of Airway Epithelia in Humans and in Old World Non-human Primates. Mol Ther. Dec. 2007;15(12):2114-23. Epub Jul. 31, 2007.
Liu et al., Comparative biology of rAAV transduction in ferret, pig and human airway epithelia. Gene Ther. Nov. 2007;14(21):1543-8. Epub Aug. 30, 2007.
Liu et al., Species-specific differences in mouse and human airway epithelial biology of recombinant adeno-associated virus transduction. Am J Respir Cell Mol Biol. Jan. 2006;34(1):56-64. Epub Sep. 29, 2005.
Lomas et al., The mechanism of Z alpha 1-antitrypsin accumulation in the liver. Nature. Jun. 18, 1992;357(6379):605-7.
Lowenstein, Crossing the rubicon. Nat Biotechnol. Jan. 2009;27(1):42-4.
Mandel et al., Recombinant adeno-associated viral vectors as therapeutic agents to treat neurological disorders. Mol Ther. Mar. 2006;13(3):463-83. Epub Jan. 18, 2006.
Manfredsson et al., AAV9: a potential blood-brain barrier buster. Mol Ther. Mar. 2009;17(3):403-5.
Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592. Rasko, John [corrected to Rasko, John JE]; Rustagi, Pradip K [added].
McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.
McCarty, Self-complementary AAV vectors; advances and applications. Mol Ther. Oct. 2008;16(10):1648-56. Epub Aug. 5, 2008.
McLean et al., Gene targeted therapeutics for liver disease in alpha-1 antitrypsin deficiency. Biologics. 2009;3:63-75. Epub Jul. 13, 2009.
Mingozzi et al., CD8(+) T-cell responses to adeno-associated virus capsid in humans. Nat Med. Apr. 2007;13(4):419-22. Epub Mar. 18, 2007.
Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.
Mueller et al., Development of Simultaneous Gene Augmentation and Reduction of Mutant Gene Expression with a Single Recombinant AAV for Alpha-1 Antitrypsin Disease. Molecular Therapy May 2009;17(1):5391-S392. Abstract 1030.
Mueller et al., In Vivo AAV Delivered Allele Specific shRNA for the Knockdown of Alpha-1 Antitrypsin. Molecular Therapy May 2010;18(1):S22. Abstract 53.
Mueller et al., In Vivo Allele Specific Knockdown of Mutant Alpha-1 Antitrypsin Using Recombinant AAV Delivered shRNA. Molecular Therapy May 2009;17(1):S313. Abstract 817.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., The pros and cons of immunomodulatory IL-10 gene therapy with recombinant AAV in a Cftr−/− -dependent allergy mouse model. Gene Ther. Feb. 2009;16(2):172-83. Epub Sep. 25, 2008.
Mueller et al., Using rAAV Delivered miRNAs to Knockdown Misfolded Human Alpha 1 Antitrypsin in a Transgenic Mouse Model. Molecular Therapy May 2010;18(1):521. Abstract 51.
O'Reilly et al., RNA interference-mediated suppression and replacement of human rhodopsin in vivo. Am J Hum Genet. Jul. 2007;81(1):127-35. Epub May 23, 2007.
Propst et al., Prevalence of hepatocellular carcinoma in alpha-1-antitrypsin deficiency. J Hepatol. Dec. 1994;21(6):1006-11.
Roy et al., Characterization of a family of chimpanzee adenoviruses and development of molecular clones for gene transfer vectors. Hum Gene Ther. May 2004;15(5):519-30.
Scallan et al., Human immunoglobulin inhibits liver transduction by AAV vectors at low AAV2 neutralizing titers in SCID mice. Blood. Mar. 1, 2006;107(5):1810-7. Epub Oct. 25, 2005.
Schnepp et al., Characterization of adeno-associated virus genomes isolated from human tissues. J Virol. Dec. 2005;79(23):14793-803.

(56) References Cited

OTHER PUBLICATIONS

Schwarz et al., Designing siRNA that distinguish between genes that differ by a single nucleotide. PLoS Genet. Sep. 8, 2006;2(9):e140, 1307-1318. Epub Jul. 24, 2006.
Seiler et al., Adeno-associated virus types 5 and 6 use distinct receptors for cell entry. Hum Gene Ther. Jan. 2006;17(1):10-9.
Sivasothy et al., Pathogenic alpha 1-antitrypsin polymers are formed by reactive loop-beta-sheet A linkage. J Biol Chem. Oct. 27, 2000;275(43):33663-8.
Song et al., Intramuscular administration of recombinant adeno-associated virus 2 alpha-1 antitrypsin (rAAV-SERPINA1) vectors in a nonhuman primate model: safety and immunologic aspects. Mol Ther. Sep. 2002;6(3):329-35.
Tomar et al., Use of adeno-associated viral vector for delivery of small interfering RNA. Oncogene. Aug. 28, 2003;22(36):5712-5.
Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vaucheret et al., The action of ARGONAUTE1 in the miRNA pathway and its regulation by the miRNA pathway are crucial for plant development. Genes Dev. May 15, 2004;18(10):1187-97. Epub May 6, 2004.
Vermeulen et al., Double-stranded regions are essential design components of potent inhibitors of RISC function. RNA. May 2007;13(5):723-30. Epub Mar. 30, 2007.
Virella-Lowell et al., Enhancing rAAV vector expression in the lung. J Gene Med. Jul. 2005;7(7):842-50.
Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.
Wu et al., Alpha2,3 and alpha2,6 N-linked sialic acids facilitate efficient binding and transduction by adeno-associated virus types 1 and 6. J Virol. Sep. 2006;80(18):9093-103.
Xia et al., Multiple shRNAs expressed by an inducible pol II promoter can knock down the expression of multiple target genes. Biotechniques. Jul. 2006;41(1):64-8.
Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.
Xie et al., Characterization of positioning effect of pol III-shRNA transcription unit in scAAV vector genome on the packaging efficiency and functionality of shRNA silencing. Molecular Therapy. May 2010;18(1): S262. Abstract 671.
Xie et al., MicroRNA regulated tissue specific transduction by rAAV vector. Molecular Therapy. May 2009;17(1): S279. Abstract 732.
Xie et al., rAAV-mediated delivery of micro RNA scavengers leads to efficient and stable knock-down of cognate micro RNAs, upregulation of their natural target genes and phenotypic changes in mice. Molecular Therapy. May 2010;18(1): S140. Abstract 362.
Yan et al., Unique biologic properties of recombinant AAV1 transduction in polarized human airway epithelia. J Biol Chem. Oct. 6, 2006;281(40):29684-92. Epub Aug. 9, 2006.
Zabner et al., Adeno-associated virus type 5 (AAV5) but not AAV2 binds to the apical surfaces of airway epithelia and facilitates gene transfer. J Virol. Apr. 2000;74(8):3852-8.
Zern et al., A novel SV40-based vector successfully transduces and expresses an alpha 1-antitrypsin ribozyme in a human hepatoma-derived cell line. Gene Ther. Jan. 1999;6(1):114-20.
Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.
Zhong et al., Chimpanzee-derived novel natural variants of aav9: vector development and interrogation of correlations between capsid structure and vector biology. Molecular Therapy. May 2010;18(1): S24. Abstract 58.

Zolotukhin et al., Production and purification of serotype 1, 2, and 5 recombinant adeno-associated viral vectors. Methods. Oct. 2002;28(2):158-67.
Alisky et al., Gene therapy for amyotrophic lateral sclerosis and other motor neuron diseases. Hum Gene Ther. Nov. 20, 2000;11(17):2315-29.
Ameres et al., Target RNA-directed tailing and trimming purifies the sorting of endo-siRNAs between the two *Drosophila* Argonaute proteins. RNA. Jan. 2011;17(1):54-63. doi: 10.1261/rna.2498411. Epub Nov. 24, 2010.
Ameres et al., Target RNA-directed trimming and tailing of small silencing RNAs. Science. Jun. 18, 2010;328(5985):1534-9. doi: 10.1126/science.1187058.
Berns et al., Biology of adeno-associated virus. Curr Top Microbiol Immunol. 1996;218:1-23.
Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.
Büssing et al., let-7 microRNAs in development, stem cells and cancer. Trends Mol Med. Sep. 2008;14(9):400-9. doi: 10.1016/j.molmed.2008.07.001. Epub Jul. 31, 2008.
Carè et al., MicroRNA-133 controls cardiac hypertrophy. Nat Med. May 2007;13(5):613-8. Epub Apr. 29, 2007.
Carter, in "Handbook of Parvoviruses", ed., P. Tijsser, CRC Press, pp. 155-168 (1990).
Chang et al., miR-122, a mammalian liver-specific microRNA, is processed from her mRNA and may downregulate the high affinity cationic amino acid transporter CAT-1. RNA Biol. Jul. 2004;1(2):106-13. Epub Jul. 1, 2004.
Choi et al., Effects of adeno-associated virus DNA hairpin structure on recombination. J Virol. Jun. 2005;79(11):6801-7.
Christensen et al., A let-7 microRNA-binding site polymorphism in the KRAS 3' UTR is associated with reduced survival in oral cancers. Carcinogenesis. Jun. 2009;30(6):1003-7. doi: 10.1093/carcin/bgp099. Epub Apr. 20, 2009.
Cideciyan et al., Human RPE65 gene therapy for Leber congenital amaurosis: persistence of early visual improvements and safety at 1 year. Hum Gene Ther. Sep. 2009;20(9):999-1004.
Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.
Curtin et al., Bidirectional promoter interference between two widely used internal heterologous promoters in a late-generation lentiviral construct. Gene Ther. Mar. 2008;15(5):384-90. doi:.10.1038/sj.gt.3303105. Epub Jan. 24, 2008.
Czech, MicroRNAs as therapeutic targets. N Engl J Med. Mar. 16, 2006;354(11):1194-5.
Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.
Davidson et al., A model system for in vivo gene transfer into the central nervous system using an adenoviral vector. Nat Genet. Mar. 1993;3(3):219-23.
Davidson et al., Recombinant adeno-associated virus type 2, 4, and 5 vectors: transduction of variant cell types and regions in the mammalian central nervous system. Proc Natl Acad Sci U S A Mar. 28, 2000;97(7):3428-32.
Daya et al., Gene therapy using adeno-associated virus vectors. Clin Microbiol Rev. Oct. 2008;21(4):583-93. doi: 10.1128/CMR.00008-08.
Di Giorgio et al., Non-cell autonomous effect of glia on motor neurons in an embryonic stem cell-based ALS model. Nat Neurosci. May 2007;10(5):608-14. Epub Apr. 15, 2007.
Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.

(56) References Cited

OTHER PUBLICATIONS

Eberling et al., Results from a phase I safety trial of hAADC gene therapy for Parkinson disease. Neurology. May 20, 2008;70(21):1980-3. doi: 10.1212/01.wnl.0000312381.29287.ff. Epub Apr. 9, 2008.
Elmén et al., Antagonism of microRNA-122 in mice by systemically administered LNA-antimiR leads to up-regulation of a large set of predicted target mRNAs in the liver. Nucleic Acids Res. Mar. 2008;36(4):1153-62. Epub Dec. 23, 2007.
Esau et al., miR-122 regulation of lipid metabolism revealed by in vivo antisense targeting. Cell Metab. Feb. 2006;3(2):87-98.
Fabani et al., miR-122 targeting with LNA/2'-O-methyl oligonucleotide mixmers, peptide nucleic acids (PNA), and PNA-peptide conjugates. RNA. Feb. 2008;14(2):336-46. Epub Dec. 11, 2007.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Forman et al., A search for conserved sequences in coding regions reveals that the let-7 microRNA targets Dicer within its coding sequence. Proc Natl Acad Sci U S A. Sep. 30, 2008;105(39):14879-84. doi: 10.1073/pnas.0803230105. Epub Sep. 23, 2008.
Gao et al., Adeno-associated virus-mediated gene transfer to nonhuman primate liver can elicit destructive transgene-specific T cell responses. Hum Gene Ther. Sep. 2009;20(9):930-42. doi: 10.1089/hum.2009.060.
Gao et al., Erythropoietin gene therapy leads to autoimmune anemia in macaques. Blood. May 1, 2004;103(9):3300-2. Epub Dec. 24, 2003.
Gentner et al., Stable knockdown of microRNA in vivo by lentiviral vectors. Nat Methods. Jan. 2009;6(1):63-6. doi: 10.1038/nmeth.1277. Epub Nov. 30, 2008.
Girard et al., miR-122, a paradigm for the role of microRNAs in the liver. J Hepatol. Apr. 2008;48(4):648-56. doi: 10.1016/j.jhep.2008.01.019. Epub Feb. 12, 2008.
Graham et al., A new technique for the assay of infectivity of human adenovirus 5 DNA. Virology. Apr. 1973;52(2):456-67.
Gramantieri et al., Cyclin G1 is a target of miR-122a, a microRNA frequently down-regulated in human hepatocellular carcinoma. Cancer Res. Jul. 1, 2007;67(13):6092-9.
Griffiths-Jones et al., miRBase: microRNA sequences, targets and gene nomenclature Nucleic Acids Res. Jan. 1; 2006;34(Database issue):D140-4.
Horwich et al., Design and delivery of antisense oligonucleotides to block microRNA function in cultured Drosophila and human cells. Nat Protoc. 2008;3(10):1537-49. doi: 10.1038/nprot.2008.145.
Hutvágner et al., Sequence-specific inhibition of small RNA function. PLoS Biol. Apr. 2004;2(4):E98. Epub Feb. 24, 2004.
Johnson et al., RAS is regulated by the let-7 microRNA family. Cell. Mar. 11, 2005;120(5):635-47.
Kaspar et al., Retrograde viral delivery of IGF-1 prolongs survival in a mouse ALS model. Science. Aug. 8, 2003;301(5634):839-42.
Kota et al., Therapeutic microRNA delivery suppresses tumorigenesis in a murine liver cancer model. Cell. Jun. 12, 2009;137(6):1005-17. doi: 10.1016/j.cell.2009.04.021.
Krützfeldt et al., Silencing of microRNAs in vivo with 'antagomirs'. Nature. Dec. 1, 2005;438(7068):685-9. Epub Oct. 30, 2005.
Kutay et al., Downregulation of miR-122 in the rodent and human hepatocellular carcinomas. J Cell Biochem. Oct. 15, 2006;99(3):671-8.
Lebherz et al., Gene therapy with novel adeno-associated virus vectors substantially diminishes atherosclerosis in a murine model of familial hypercholesterolemia. J Gene Med. Jun. 2004;6(6):663-72.
Lewis et al., Conserved seed pairing, often flanked by adenosines, indicates that thousands of human genes are microRNA targets. Cell. Jan. 14, 2005;120(1):15-20.
Lewis et al., Prediction of mammalian microRNA targets. Cell. Dec. 26, 2003 ;115(7):787-98.
Loya et al., Transgenic microRNA inhibition with spatiotemporal specificity in intact organisms Nat Methods. Dec. 2009;6(12):897-903. doi: 10.1038/nmeth.1402. Epub Nov. 15, 2009.
Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.
Martin-Duque et al., Direct comparison of the insulating properties of two genetic elements in an adenoviral vector containing two different expression cassettes. Hum Gene Ther. Oct. 2004;15(10):995-1002.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
Meister et al., Sequence-specific inhibition of microRNA- and siRNA-induced RNA silencing. RNA. Mar. 2004;10(3):544-50.
Rayner et al., MiR-33 contributes to the regulation of cholesterol homeostasis. Science. Jun. 18, 2010;328(5985):1570-3. doi: 10.1126/science.1189862. Epub May 13, 2010.
Sambrook et al, "Molecular Cloning. A Laboratory Manual", 2d ed., Cold Spring Harbor Laboratory, New York (1989). 16.
Sen et al., Micromanaging vascular biology: tiny microRNAs play big band. J Vasc Res. 2009;46(6):527-40. doi: 10.1159/000226221. Epub Jun. 30, 2009.
Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.
Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.
Waldman et al., Applications of microRNA in cancer: Exploring the advantages of miRNA. Clin Transl Sci. Jun. 2009;2(3):248-9. doi: 10.1111/j.1752-8062.2009.00110.x.
Wu et al., Nerve injection of viral vectors efficiently transfers transgenes into motor neurons and delivers RNAi therapy against ALS. Antioxid Redox Signal. Jul. 2009;11(7):1523-34.
Xia et al., Allele-specific RNAi selectively silences mutant SOD1 and achieves significant therapeutic benefit in vivo. Neurobiol Dis. Sep. 2006;23(3):578-86. Epub Jul. 20, 2006.
Yang et al., The muscle-specific microRNA miR-1 regulates cardiac arrhythmogenic potential by targeting GJA1 and KCNJ2. Nat Med. Apr. 2007;13(4):486-91. Epub Apr. 1, 2007. Erratum in: Nat Med. Dec. 2011;17(12):1693.
Yu et al., let-7 regulates self renewal and tumorigenicity of breast cancer cells. Cell. Dec. 14, 2007;131(6):1109-23.
Genbank Submission; Accession No. ADZ26851; Wilson et al.; Jun. 30, 2005.
Haraguchi et al., Vectors expressing efficient RNA decoys achieve the long-term suppression of specific microRNA activity in mammalian cells. Nucleic Acids Res. Apr. 2009;37(6):e43. doi: 10.1093/nar/gkp040. Epub Feb. 17, 2009.
Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].
Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.
Foust et al., Rescue of the spinal muscular atrophy phenotype in a mouse model by early postnatal delivery of SMN. Nat Biotechnol. Mar. 2010;28(3):271-4. doi: 10.1038/nbt.1610. Epub Feb. 28, 2010.
Kumar et al., Canavan disease: a white matter disorder. Ment Retard Dev Disabil Res Rev. 2006;12(2):157-65.
Loiler et al., Targeting recombinant adeno-associated virus vectors to enhance gene transfer to pancreatic islets and liver. Gene Ther. Sep. 2003;10(18):1551-8.
Matalon et al., Adeno-associated virus-mediated aspartoacylase gene transfer to the brain of knockout mouse for canavan disease. Mol Ther. May 2003;7(5 Pt 1):580-7.
Naldini, Ex vivo gene transfer and correction for cell-based therapies. Nat Rev Genet. May 2011;12(5):301-15. doi: 10.1038/nrg2985. Epub Mar. 29, 2011.

(56) References Cited

OTHER PUBLICATIONS

Sondhi et al., Enhanced survival of the LINCL mouse following CLN2 gene transfer using the rh.10 rhesus macaque-derived adeno-associated virus vector. Mol Ther. Mar. 2007;15(3):481-91. Epub Dec. 19, 2006.
Tenenbaum et al., Recombinant AAV-mediated gene delivery to the central nervous system. J Gene Med. Feb. 2004;6 Suppl 1:S212-22.
Véniant et al., Lipoprotein clearance mechanisms in LDL receptor-deficient "Apo-B48-only" and "Apo-B100-only" mice. J Clin Invest. Oct. 15, 1998;102(8):1559-68.
Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.
Xie et al., MicroRNA-regulated, systemically delivered rAAV9: a step closer to CNS-restricted trangene expression. Mol Ther. Mar. 2011;19(3):526-35. doi: 10-1038/mt.2010.279. Epub Dec. 21, 2010.
Arbuthnot et al., Hepatic delivery of RNA interference activators for therapeutic application. Curr Gene Ther. Apr. 2009;9(2):91-103.
Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.
Conlon et al., Ribozyme Approaches towards Down-Regulation of Pi*Z Mutant Human a-1 Anti-Trypsin. Mol. Therapy. 2004;9:S333.
Cruz et al., the promise of gene therapy for the treatment of alpha-1 antitrypsin deficiency. Pharmacogenomics. Sep. 2007;8(9):1191-8.
Elmen et al., LNA-mediated microRNA silencing in non-human primates. Nature. Apr. 17, 2008;452(7189):896-9. Epub Mar. 26, 2008.
Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Lynn, Meta-regulation: microRNA regulation of glucose and lipid metabolism. Trends Endocrinol Metab. Nov. 2009;20(9):452-9. doi: 10.1016/j.tem.2009.05.007. Epub Sep. 30, 2009.
Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Wang et al., The design of vectors for RNAi delivery system. Curr Pharm Des. 2008;14(13):1327-40.
Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.
Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.
Kumar et al., Lack of aspartoacylase activity disrupts survival and differentiation of neural progenitors and oligodendrocytes in a mouse model of Canavan disease. J Neurosci Res. Nov. 15, 2009;87(15):3415-27. doi: 10.1002/jnr.22233.

* cited by examiner

LIVING IMAGE DATA, EXPOSURE TIME: 0.5s
4 WEEKS AFTER rAAV9 INJECTION BY IV, DOSE = VECTOR GENOME COPIES/MOUSE
VECTOR: rAAV9CB.FFLuc.7XLet7 SPONGE OR rAAV9CB.FFLuc.7X Let7-MUTANT SPONGE

STRUCTURES OF THE mi122 SPONGE AND MUTANT SPONGE

```
                    ACAG          UGUGAGGU-5'
miR-122: 3'- GUUUGUGGUA
miR-122 SPONGE: 5'- CAAACACCAT    ACACTCCA-3'
                    ACA

ACAG    GAGGU   -5'
miR-122: 3'- GUUUGUGGUA  UGU
MutmiR-122 SPONGE: 5'- CAAACACCAT  ACA     -3'
                                   ACA  AGAAA
```

7XmiR-122 SPONGE SEQUENCE:
caaacaccatacaacactcccaaacaccatacaacactcccaaacaccatacaacactccacaaacaccatacaacactccacaaacaccatacaacactccacaaacaccatacaacactccacaaacaccatacaacactcca

Fig. 7

LET-7 SPONGE DESIGN

```
                    GGAU
LET-7b: 3'- UUGGUGUGUU      GAUGGAGU-5'
Let-7b SPONGE: 5'- AACCACACAA    CTACCTCA-3'
                           AAC

GGAGU
Let-7b: 3'- UUGGUGUGUU   GAU      -5'
MUTLET-7b SPONGE: 5'- AACCACACAA   CTA    -3'
                                 AAC  AAGAA
```

7XLet-7 SPONGE SEQUENCE:

aactatacaaacctacctcaaactacaaccacacaaaacctacctcaaactatacaaaacctacctcaaactgtaacaaactatgtacaaaacctacctcaaactataccaaaacctacctcaaactgtacaaaacctacctcaaactataccaaaacctacctca

Fig. 14

```
                        SEQUENCE LISTING

<160> NUMBER OF SEQ ID NOS: 20

<210> SEQ ID NO 1
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n is a, c, g, t or absent
<220> FEATURE:
<221> NAME/KEY: misc_feature
<222> LOCATION: (27)..(27)
<223> OTHER INFORMATION: n is a, c, g, t or absent

<400> SEQUENCE: 1
ngaytgyvwh wykgarcaat aaatgan                                          27

<210> SEQ ID NO 2
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n is a, c, g, t or absent
<220> FEATURE:
<221> NAME/KEY: misc_feature
<222> LOCATION: (30)..(30)
<223> OTHER INFORMATION: n is a, c, g, t or absent

<400> SEQUENCE: 2
ngaaacgaat haamcggttt attgattaan                                       30

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
gactgtgttt ctgagcaata aatga                                            25

<210> SEQ ID NO 4
<211> LENGTH: 28
<212> TYPE: DNA
<213> ORGANISM: Artificial Sequence
<220> FEATURE:
<223> OTHER INFORMATION: Primer

<400> SEQUENCE: 4
gaaacgaatt aaccggttta ttgattaa                                         28

<210> SEQ ID NO 5
<211> LENGTH: 24
<212> TYPE: DNA
<213> ORGANISM: Artificial Sequence
<220> FEATURE:
<223> OTHER INFORMATION: Primer
```

```
<220> FEATURE:
<221> NAME/KEY: misc_feature
<222> LOCATION: (1)..(1)
<223> OTHER INFORMATION: n is a, c, g, t or absent
<220> FEATURE:
<221> NAME/KEY: misc_feature
<222> LOCATION: (24)..(24)
<223> OTHER INFORMATION: n is a, c, g, t or absent

<400> SEQUENCE: 5
nymrwmrwck ksagamgcgg rmsn                                        24

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
ccatcgacgt cagacgcgga ag                                          22

<210> SEQ ID NO 7
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n is a, c, g, t or absent
<220> FEATURE:
<221> NAME/KEY: misc_feature
<222> LOCATION: (26)..(26)
<223> OTHER INFORMATION: n is a, c, g, t or absent

<400> SEQUENCE: 7
nssvgacrss tmscarwwca raygtn                                      26

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
gccgacaggt accaaaacaa atgt                                        24

<210> SEQ ID NO 9
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n is a, c, g, t or absent
<220> FEATURE:
<221> NAME/KEY: misc_feature
<222> LOCATION: (24)..(24)
<223> OTHER INFORMATION: n is a, c, g, t or absent

<400> SEQUENCE: 9
nmyggmrygt sarwatytsa aycn                                        24

<210> SEQ ID NO 10
```

```
<211> LENGTH: 22
<212> TYPE: DNA
<213> ORGANISM: Artificial Sequence
<220> FEATURE:
<223> OTHER INFORMATION: Primer

<400> SEQUENCE: 10
ccggcgtgtc agaatctcaa cc                                              22

<210> SEQ ID NO 11
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n is a, c, g, t or absent
<220> FEATURE:
<221> NAME/KEY: misc_feature
<222> LOCATION: (10)..(10)
<223> OTHER INFORMATION: n is a, c, g, t or absent
<220> FEATURE:
<221> NAME/KEY: misc_feature
<222> LOCATION: (31)..(31)
<223> OTHER INFORMATION: n is a, c, g, t or absent

<400> SEQUENCE: 11
nacrbragan ccaaagttca actgamacga n                                    31

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12
acaggagacc aaagttcaac tgaaacga                                        28

<210> SEQ ID NO 13
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 13
uggaguguga caauguguu ug                                               22

<210> SEQ ID NO 14
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 14
caaacaccat acaacactcc a                                               21

<210> SEQ ID NO 15
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 15
```
caaacaccat acaacaagaa a                                                    21

<210> SEQ ID NO 16
<211> LENGTH: 146
<212> TYPE: DNA
<213> ORGANISM: Artificial Sequence
<220> FEATURE:
<223> OTHER INFORMATION: Synthetic Oligonucleotide

<400> SEQUENCE: 16
caaacaccat acaacactcc acaaacacca tacaacactc cacaaacacc atacaacact          60
ccacaaacac catacaacac tccacaaaca ccatacaaca ctccacaaac accatacaac         120
actccacaac accatacaac actcca                                             146

<210> SEQ ID NO 17
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 17
ugagguagua gguugugugg uu                                                   22

<210> SEQ ID NO 18
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 18
aaccacacaa aacctacctc a                                                    21

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 19
aaccacacaa aacctaaaga a                                                    21

<210> SEQ ID NO 20
<211> LENGTH: 146
<212> TYPE: DNA
<213> ORGANISM: Artificial Sequence
<220> FEATURE:
<223> OTHER INFORMATION: Synthetic Oligonucleotide

<400> SEQUENCE: 20
aactatacaa aacctacctc aaccacacaa aacctacct caaaccatac aaaacctacc           60
tcaaactatg caaaacctac ctctaactat acaaaaccta cctcaaactg tacaaaacct         120
acctcaacca tacaaaacct acctca                                             146

ISOLATION OF NOVEL AAV'S AND USES THEREOF

RELATED APPLICATIONS

The present application is a continuation-in-part of U.S. Non-Provisional patent application Ser. No. 12/473,917 filed on May 28, 2009, entitled "Isolation of Novel AAV's and Uses Thereof", which claims priority under 35 U.S.C. §119 (e) to U.S. provisional application, U.S. Ser. No. 61/130,105, filed May 28, 2008, the contents of which are incorporated herein by reference in their entireties.

FEDERALLY SPONSORED RESEARCH

This invention was made with government support under grant nos. HL059407 and DK047757 awarded by the National Institutes of Health. The government has certain rights in the invention.

FIELD OF THE INVENTION

The invention in some aspects relates to isolated nucleic acids, compositions, and kits useful for identifying adeno-associated viruses in cells. In some aspects, the invention provides methods for identifying adeno-associated viruses in cells based on the detection of AAV RNA in the cells. In some aspects the invention provides methods for producing somatic transgenic animal models using recombinant AAV with tissue targeting capabilities.

BACKGROUND OF INVENTION

Adenoassociated Virus (AAV) is a small and helper dependent virus. It was discovered in 1960s as a contaminant in adenovirus (a cold causing virus) preparations. Its growth in cells is dependent on the presence of adenovirus and, therefore, it was named as adeno-associated virus. Before 2002, a total of 6 serotypes of AAVs were identified, including the serotype 2 which was the first AAV developed as vector for gene transfer applications and the one used in the recent break through eye gene therapy trials. In the earlier attempts to develop AAV as gene transfer vehicle, prototype AAV vector based on serotype 2 effectively served as a proof-of-concept showcase and accomplished non-toxic and stable gene transfer in murine and large animal models in different target tissues. For instance an 8 year stable vision improvement was observed in a dog model of LCA after a single injection and a 9 year stable gene expression in Macaque muscle was achieved. However, these proof-of-concept studies also revealed a significant shortcoming which is a poor gene transfer efficiency in major target tissues.

Methods for discovering novel AAVs have been largely focused on isolating DNA sequences for AAV capsids, which relate to the tissue targeting capacity of the virus. To date, the principal methods employed for identifying novel AAV take advantage of the latency of AAV proviral DNA genomes and focus on rescuing persisted viral genomic DNA. The major challenge in DNA-targeted AAV isolation is that the abundance of persisted AAV genomes is often very low in most of tissues particularly in human tissues, which makes AAV rescue unachievable in many cases.

SUMMARY OF INVENTION

In some aspects, the invention relates to the use of AAV based vectors as vehicles for the development somatic transgenic animal models. In some aspects, the invention relates to AAV serotypes that have demonstrated distinct tissue/cell type tropism and can achieve stable somatic gene transfer in animal tissues at levels similar to those of adenoviral vectors (e.g., up to 100% in vivo tissue transduction depending upon target tissue and vector dose) in the absence of vector related toxicology. In other aspects, the invention relates to AAV serotypes having liver, heart and pancreas tissue targeting capabilities. These tissues are associated with a broad spectrum of human diseases including a variety of metabolic, cardiovascular and diabetic diseases. Thus, in some aspects the invention relates to the use of adeno-associated virus based vector as a vehicle for the development somatic transgenic animal models of human diseases such as metabolic, cardiovascular, and diabetic disease.

Availability of appropriate animal models for further understanding pathogenesis and developing therapeutics for those diseases is a major challenge in biomedical research. The methods for generating the somatic models, as described herein, avoid the time consuming and costly process of germ line gene transfer and cogenic breeding for each target gene of transgenic animals as well as some embryonic lethal consequences, and provide versatility to create animal models from, for example, different strains, genetic background, or at different ages. The somatic animal models of the invention provide an important system for studying pathogenesis of diseases and consequences of abnormal gene expression in various tissue.

In other aspects the invention relates to methods involving administering a recombinant Adeno-Associated Virus (rAAV) to a subject, wherein the rAAV infects cells of a target tissue of the subject, and wherein the rAAV is at least one transgene that expresses a small interfering nucleic acid. The subject may be, for instance, an animal such as a somatic transgenic animal model.

In some embodiments the small interfering nucleic acid is an miRNA. The small interfering nucleic acid may be an miRNA sponge that inhibits the activity of at least one miRNA in the animal. For instance, the miRNA is an endogenous miRNA. In some embodiments the miRNA is expressed in a cell of the target tissue, optionally wherein the target tissue is heart, liver, or pancreas. In other embodiments the transgene expresses a transcript that comprises at least one binding site for a miRNA, wherein the miRNA inhibits activity of the transgene, in a tissue other than the target tissue, by hybridizing to the binding site.

In some aspects a method is provided that involves administering a recombinant Adeno-Associated Virus (rAAV) to a subject, wherein the rAAV comprises at least one transgene, wherein the transgene expresses a transcript that comprises at least one binding site for a miRNA, wherein the miRNA inhibits activity of the transgene, in a tissue other than a target tissue, by hybridizing to the binding site of the transcript.

In other aspects, a method for generating a somatic transgenic animal model by administering a recombinant Adeno-Associated Virus (rAAV) to an animal, wherein the rAAV comprises at least one transgene, wherein the transgene expresses a transcript that comprises at least one binding site for a miRNA, wherein the miRNA inhibits activity of the transgene, in a tissue other than a target tissue, by hybridizing to the binding site of the transcript is provided.

In some embodiments of the methods provided herein the transgene is a tissue specific promoter or inducible promoter. The tissue specific promoter may be, for instance, a liver-specific thyroxin binding globulin (TBG) promoter, a insulin promoter, a glucagon promoter, a somatostatin promoter, a pancreatic polypeptide (PPY) promoter, a synapsin-1 (Syn)

promoter, a creatine kinase (MCK) promoter, a mammalian desmin (DES) promoter, a α-myosin heavy chain (a-MHC) promoter, or a cardiac Troponin T (cTnT) promoter.

In some embodiments the rAAV has a capsid from an AAV serotype selected from: AAV1, AAV2, AAV3, AAV4, AAV5, AAV6, AAV7, AAV8, AAV9, AAV10, AAV11, and AAV12. In other embodiments the rAAV is a variant of an AAV serotype selected from: AAV1, AAV2, AAV3, AAV4, AAV5, AAV6, AAV7, AAV8, AAV9, AAV10, AAV11, and AAV12. In yet other embodiments the rAAV has an Inverted Terminal Repeat (ITR) sequence from an AAV serotype selected from: AAV1, AAV2, AAV3, AAV4, AAV5, AAV6, AAV7, AAV8, AAV9, AAV10, AAV11, and AAV12.

The target tissue may be any tissue such as gonad, diaphragm, heart, stomach, liver, spleen, pancreas, or kidney. The rAAV may transduces any type of tissue, for example, muscle fibers, squamous epithelial cells, renal proximal or distal convoluted tubular cells, mucosa gland cells, blood vessel endothelial cells, or smooth muscle cells.

In some embodiments a dose of $10^{10}$, $10^{11}$, $10^{12}$, or $10^{13}$ genome copies is administered.

In other embodiments the methods of administering are performed intravenously, or through the portal vein of the animal.

In some embodiments the subject is a human or an animal, wherein the animal is a mammal, optionally wherein the mammal is selected from a mouse, a rat, a rabbit, a dog, a cat, a sheep, a pig, a non-human primate.

The transgene may express, for instance, a cancer related gene, an apoptosis-related gene, or a pro-apoptotic gene.

In some embodiments the transgene causes a pathological state in the animal.

The method may also include the step of administering a putative therapeutic agent to the somatic transgenic animal model to determine the effect of the putative therapeutic agent on the pathological state in the animal.

In some embodiments the transgene expresses a reporter gene. The reporter gene may be a reporter enzyme, optionally which is Beta-Galactosidase or a Fluorescent protein, optionally which is GFP.

In some embodiments the transgene expresses a transcript that comprises binding sites for different microRNAs that are endogenously expressed in different cells of the animal and that inhibit activity of the transgene in different tissues.

A somatic transgenic animal produced by the method described herein is also provided according to the invention.

A kit for producing a rAAV that generates a somatic transgenic animal that expresses a transgene in a target tissue is provided according to other aspects of the invention. The kit includes at least one container housing a recombinant AAV vector, wherein the recombinant AAV vector comprises a transgene that expresses a small interfering nucleic acid and/or expresses a transcript that comprises at least one binding site for a miRNA, wherein the miRNA inhibits activity of the transgene, in a tissue other than the target tissue, by hybridizing to the binding site of the transcript, at least one container housing a rAAV packaging component, and instructions for constructing and packaging the rAAV, wherein the rAAV transduces cells of the target tissue.

In some embodiments a rAAV packaging component includes a host cell expressing at least one rep gene and/or at least one cap gene.

In other embodiments the host cell is a 293 cell.

The host cell, in some embodiments, expresses at least one helper virus gene product that effects the production of rAAV containing the recombinant AAV vector. The at least one cap gene may encode a capsid protein from an AAV serotype that binds to cells of the target tissue.

In some embodiments the AAV serotype is selected from: AAV1, AAV2, AAV3, AAV4, AAV5, AAV6, AAV7, AAV8, AAV9, AAV10, AAV11, and AAV12. In other embodiments the AAV serotype is a variant of an AAV serotype selected from: AAV1, AAV2, AAV3, AAV4, AAV5, AAV6, AAV7, AAV8, AAV9, AAV10, AAV11, and AAV12. In yet other embodiments the rAAV has an Inverted Terminal Repeat (ITR) sequence from an AAV serotype selected from: AAV1, AAV2, AAV3, AAV4, AAV5, AAV6, AAV7, AAV8, AAV9, AAV10, AAV11, and AAV12.

In some embodiments a rAAV packaging component includes a helper virus optionally wherein the helper virus is an adenovirus or a herpes virus.

The target tissue may be any tissue such as gonad, diaphragm, heart, stomach, liver, spleen, pancreas, or kidney. The rAAV may transduces any type of tissue, for example, muscle fibers, squamous epithelial cells, renal proximal or distal convoluted tubular cells, mucosa gland cells, blood vessel endothelial cells, or smooth muscle cells.

The transgene may express, for instance, a cancer related gene, an apoptosis-related gene, or a pro-apoptotic gene.

In some embodiments the small interfering nucleic acid is an miRNA. The small interfering nucleic acid may be an miRNA sponge, wherein miRNA sponge inhibits the activity of one or more miRNAs in the somatic transgenic animal.

In other embodiments the miRNA is an endogenous miRNA of the animal. The miRNA may be expressed in a cell of a heart, liver, or pancreas tissue in the somatic transgenic animal.

In some embodiments the transgene expresses a toxin and/or a reporter gene. The reporter gene may be a reporter enzyme, optionally which is Beta-Galactosidase or a Fluorescent protein, optionally which is GFP.

In some embodiments the transgene includes a tissue specific promoter or inducible promoter. The tissue specific promoter may be a liver-specific thyroxin binding globulin (TBG) promoter, a insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1 depicts the results of an assessment of the ability of rAAVs to deliver transgenes that are susceptible to miRNA targeting and degradation.

FIG. 7 shows the structure of miR122 sponge sequences, which where incorporated into rAAV-9-based miR-122 sponge delivery vectors. SEQ ID NO: 13 corresponds to miR-133; SEQ ID NO: 14 corresponds to miR-122 sponge; SEQ ID NO: 15 corresponds to MutmiR-122 sponge; and SEQ ID NO: 16 corresponds to 7xmiR-122 sponge.

FIG. 11 depicts primer design and PCR analysis in mice of lacZ mRNA.

FIG. 14 depicts a Let-7 sponge design. SEQ ID NO: 16 corresponds to Let-7b; SEQ ID NO: 17 corresponds to Let-7b sponge; SEQ ID NO: 18 corresponds to MutLet-7b sponge; and SEQ ID NO: 19 corresponds to 7xLet-7b sponge.

DETAILED DESCRIPTION

Figure 1A:
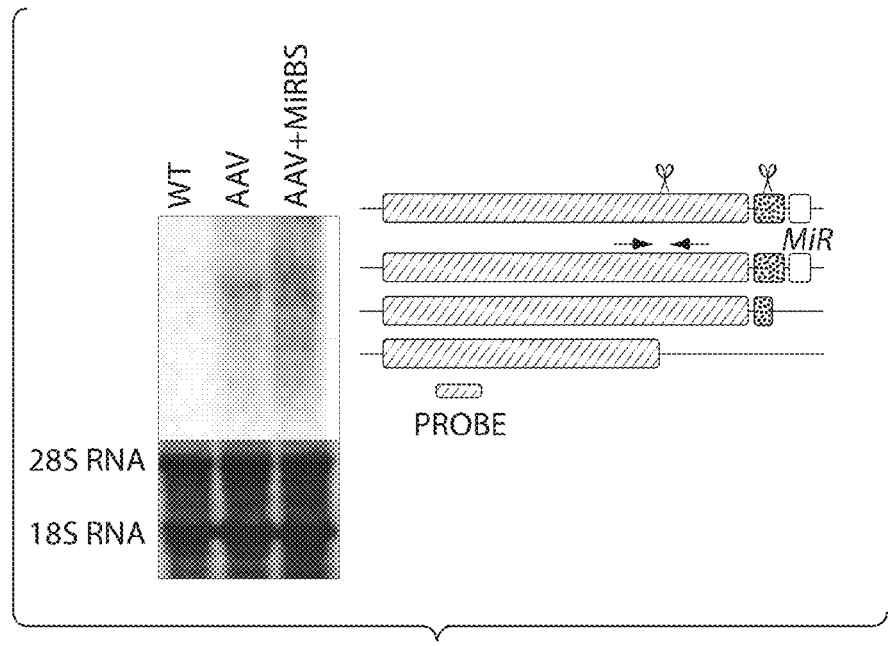
FIG. 1A depicts multiple AAV expression constructs. Schematics of transcript length and cleavage products are shown next to bands which correspond to AAV+miRBS.

Adeno-associated virus (AAV) is a small (20 nm) replication-defective, nonenveloped virus, that depends on the presence of a second virus, such as adenovirus or herpes virus, for its growth in cells. AAV is not known to cause disease and induces a very mild immune response. AAV can infect both dividing and non-dividing cells and may incorporate its genome into that of the host cell. These features make AAV a very attractive candidate for creating viral vectors for gene therapy. Prototypical AAV vectors based on serotype 2 provided a proof-of-concept for non-toxic and stable gene transfer in murine and large animal models, but exhibited poor gene transfer efficiency in many major target tissues. The invention in some aspects seeks to overcome this shortcoming by providing methods for identifying novel AAVs having distinct tissue targeting capabilities for gene therapy and research applications.

The biology of AAV vector is primarily dictated by its capsid. Consequently, methods for discovering novel AAVs have been largely focused on isolating DNA sequences for AAV capsids. To date, the primary methods used for isolating novel AAV include PCR based molecular rescue of latent AAV DNA genomes, infectious virus rescue of latent proviral genome from tissue DNAs in vitro in the presence of adenovirus helper function, and rescue of circular proviral genome from tissue DNAs by rolling-circle-linear amplification, mediated by an isothermal phage Phi-29 polymerase. All of these isolation methods take advantages of the latency of AAV proviral DNA genomes and focus on rescuing persisted viral genomic DNA. The major challenge in DNA-targeted AAV isolation is that the abundance of persisted AAV genomes is often very low in most tissues particularly in human tissues, which makes AAV rescue unachievable in many cases.

The invention in some aspects is based on the surprising discovery that endogenous latent AAV genomes are transcriptionally active in mammalian cells (e.g., cells of nonhuman primate tissues such as liver, spleen and lymph nodes). A central feature of the adeno-associated virus (AAV) latent life cycle is persistence in the form of integrated and/or episomal genomes in a host cell. However, prior to the instant invention it was not known whether AAVs express viral genes (e.g., rep and cap genes) during latency (i.e., in a latent state).

As disclosed herein, both rep and cap gene transcripts are detected with variable abundances by RNA detection methods (e.g., RT-PCR). Presence of cap gene transcripts and ability to generate cDNA of cap RNA through reverse transcription (RT) in vitro significantly increase abundance of templates for PCR-based rescue of novel cap sequences from tissues and enhance the sensitivity of novel AAV recovery. In some aspects, the methods of the invention involve transfecting cells with total cellular DNAs isolated from the tissues that potentially harbor proviral AAV genomes at very low abundance and supplementing with helper virus function (e.g., adenovirus) to trigger and/or boost AAV rep and cap gene transcription in the transfected cells. In some cases, RNA from the transfected cells provides a template for RT-PCR amplification of cDNA, for example, cap cDNA.

Thus, the invention provides methods for detecting an adeno-associated virus (AAV) in a cell based on the detection of an RNA in the cell that is indicative of the presence of the adeno-associated virus in the cell. The cell may be obtained from any number of sources such as from a tissue, saliva, gingival secretions, cerebrospinal fluid, gastrointestinal fluid, mucus, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, and nasal secretions. In some specific cases, the cell is from liver, spleen, or lymph node tissue. The cells may be obtained from any number of sources using methods well known in the art.

RNA may be isolated from a cell (preferably a cell known to have a latent AAV infection) and using any number of appropriate methods to detect the RNA, such as those described below. For the purposes of identifying novel AAVs it is useful to employ any RNA detection method known in the art that produces sequence information about the RNA. The sequence information can then be used to identify the AAV.

Typically, the isolated RNA is reverse transcribed to produce cDNA. The cDNA can then be easily manipulated to obtain sequence information about the template RNA. For example, in some cases the cDNA can be cloned into any appropriate vector plasmid (e.g., cloning plasmid) and amplified (e.g., in bacteria). The cloned cDNA can then be purified and sequenced using methods well known in the art.

Still other RNA detection methods are useful in the current invention. For example, the invader assay has been developed to detect RNA molecules, using a two-step FRET-based invader assay (Kwiatkowski, R. W., Lyamichev, V., de Arruda, M. and Neri, B. (1999) Clinical, genetic, and pharmacogenetic applications of the Invader assay. Mol Diagn, 4(4), 353-64.). High-throughput parallel analyses of many RNA transcripts are possible with DNA microarray technology. Padlock probes are useful to detect single-nucleotide variants in RNA. Serial analysis of gene expression (SAGE) is another approach. Other approaches will be apparent to the skilled artisan.

In some embodiments, isolated RNA from a cell having a latent AAV is reverse transcribed to produce cDNA. The cDNA is then subjected to a PCR reaction to amplify a target sequence of interest. Any number of PCR methods known in the art may be appropriate including, for example, Allele specific PCR, Asymmetric PCR, Solid Phase PCR, TAIL-PCR: Thermal asymmetric interlaced PCR, Hot-start PCR, Touchdown PCR, Inverse PCR, Linear PCR, Ligation-mediated PCR, Multiplex-PCR, Nested PCR, and Quantitative PCR (Q-PCR) (e.g., Taqman, SYBR green).

Typically, the target sequence of the PCR has useful information about the AAV serotype. The target sequence may span about 100 by to about 2.8 kilobase pairs in length. It is particularly desirable that the target sequence is sufficiently unique to positively identify the amplified sequence as being from a particular AAV serotype. For example, in one embodiment, the target sequence is about 250 by in length, and is sufficiently unique among known AAV sequences, that it positively identifies the amplified region as being of AAV unique origin. Typically the target sequence will contain a variable sequence (e.g., AAV hypervariable region) that is sufficiently unique that can be used to identify the AAV serotype from which the amplified sequences originate. Once amplified (and thereby detected), the sequences can be identified by performing conventional restriction digestion and comparison to restriction digestion patterns for this region in any of AAV 1, AAV2, AAV3, AAV4, AAV5, AAV6, AAV7, AAV8, AAV9, AAV10, AAV11, AAV12, or any other known or novel serotypes. The skilled artisan will appreciate that the sequences of known serotypes can be obtained from various publicly accessible databases including for example GenBank. In preferred embodiments, the amplified (and thereby detected) target sequences are identified by sequencing and comparing the obtained sequence to known AAV1, AAV2, AAV3, AAV4, AAV5, AAV6, AAV7, AAV8, AAV9, AAV10, AAV11, AAV 12 serotypes, or any other novel serotypes.

The invention, thus, includes isolated nucleic acids useful for identifying novel AAV sequences. Typically, the isolated nucleic acids are used as primers in reverse transcription and/or polymerase chain reactions. Examples of primers useful in a reverse transcription reaction include OligodT, random hexamers, and the sequence specific primers disclosed herein (e.g., SEQ ID NO 1, SEQ ID NO: 2, SEQ ID NO: 3, SEQ ID NO: 4). Other primers appropriate for a reverse transcription reaction are known in the art. Nucleic acids of the invention which are useful as PCR primers may have a sequence that has substantial homology with a nucleic acid sequence of a region that is highly conserved between at least two AAV serotypes. In some cases, the region is highly conserved between two, three, four, five, six, seven, eight, nine, ten, eleven, or twelve or more AAV serotypes. Typically, the region that is highly conserved covers an end-to-end length of between 25 and 250 bp. In specific cases, the region covers about 150 bp. However, in other cases the end-to-end length of the highly conserved region is greater that 250 bp. Preferably, the region is highly conserved within this end-to-end length over at least about 9, and more preferably, at least 18 base pairs (bp). However, the region may be conserved over more than 18 bp, more than 25 bp, more than 30 bp, or more than 50 bp.

The term "substantial homology", when referring to a nucleic acid, or fragment thereof, indicates that, when optimally aligned with appropriate nucleotide insertions or deletions with another nucleic acid (or its complementary strand), there is nucleotide sequence identity in about 90 to 100% of the aligned sequences.

The term "highly conserved" means at least 80% identity, preferably at least 90% identity, and more preferably, over 97% identity. In some cases, highly conserved may refer to 100% identity. Identity is readily determined by one of skill in the art by, for example, the use of algorithms and computer programs known by those of skill in the art.

As described herein, alignments are performed using any of a variety of publicly or commercially available Multiple Sequence Alignment Programs, such as "Clustal W", accessible through Web Servers on the internet. Alternatively, Vector NTI utilities are also used. There are also a number of algorithms known in the art which can be used to measure nucleotide sequence identity, including those contained in the programs described above. As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Similar programs are available for amino acid sequences, e.g., the "Clustal X" program. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs.

Typically, the AAV serotypes (e.g., at least two) are selected from AAV1, AAV2, AAV3, AAV4, AAV5, AAV6, AAV7, AAV8, AAV9, AAV10, AAV11, and AAV12. However, the invention is not so limited and other appropriate AAV serotypes (and subtypes) will be apparent to one of ordinary skill in the art.

In some cases, an isolated nucleic acid of the invention is a primer that has substantial homology with a nucleic acid sequence corresponding to a 5' or 3' untranslated region of a transcript (e.g., mRNA) of an AAV. AAV genes include the cap proteins, including the VP1, VP2, VP3, and the rep proteins, including Rep78, Rep68, Rep52, and Rep40. The overlapping sequences of three capsid proteins, VP1, VP2 and VP3, are generally understood to be transcribed from one promoter, designated p40. Whereas, two promoters identified as p5 and p19, are understood to produce transcripts encoding Rep78, Rep68, Rep52 and Rep40. Thus, in some cases, an isolated nucleic acid of the invention (e.g., primer) comprises a nucleic acid sequence that has substantial homology with a nucleic acid sequence corresponding to a 5' or 3' untranslated region of a p5, p19, or p40 initiated transcript (i.e., mRNA) of an AAV. The primer may be, for instance, a nucleic acid sequence that has substantial homology with a nucleic acid sequence corresponding to a 5' untranslated region of a p40 initiated transcript (i.e., Cap gene mRNA) of an AAV. Alternatively, the primer may be a nucleic acid sequence that has substantial homology with a nucleic acid sequence corresponding to a 3' untranslated region of a p40 initiated transcript (i.e., Cap gene mRNA) of an AAV. In some embodiments the primers have a sequence as set forth in Table 1.

TABLE 1

AAV CAP GENE PRIMERS

| SEQ ID | | NUCLEIC ACID SEQUENCE |
|---|---|---|
| SEQ ID NO: 1 | CapF-X | (A/G/C/T/absent)GA(C/T)TG (C/CT)(A/G/C)(A/T)(C/T/A) (A/T)(C/T)(G/T)GA(A/G)CAATA AATGA(A/G/C/T/absent) |
| SEQ ID NO: 1- (single letter code) | CapF-X | NGAYTGYVWHWYKGARCAATAAATGAN |

TABLE 1-continued

AAV CAP GENE PRIMERS

| SEQ ID | | NUCLEIC ACID SEQUENCE |
|---|---|---|
| SEQ ID NO: 2 | CapR-X | (A/G/C/T/absent)GAAACGAAT (C/A/T)AA(C/A)CGGTTTATTGATT AA(A/G/C/T/absent) |
| SEQ ID NO: 2- (single letter code) | CapR-X | NGAAACGAATHAAMCGGTTTATTGATT AAN |
| SEQ ID NO: 3 | CapF | GACTGTGTTTCTGAGCAATAAATGA |
| SEQ ID NO: 4 | CapR | GAAACGAATTAACCGGTTTATTGATTA A |
| SEQ ID NO: 5 | CapF22-X | (A/G/C/T/absent)(C/T)(C/A) (A/G)(T/A)(C/A)(A/G)(A/T)C (G/T)(G/T)(G/C)AGA(A/C)GCGG (A/G)(NC)(G/C)(A/G/C/T/ absent) |
| SEQ ID NO: 5 (single letter code) | CapF22-X | NYMRWMRWCKKSAGAMGCGGRMSN |
| SEQ ID NO: 6 | CapF22 | CCATCGACGTCAGACGCGGAAG |
| SEQ ID NO: 7 | CapF64-X | (A/G/C/T/absent)(G/C)(G/C) (C/A/G)GAC(A/G)(G/C)(G/C)T (A/C)(G/C)CA(A/G)(A/T)(A/T) CA(A/G)A(T/C)GT(A/G/C/T/ absent) |
| SEQ ID NO: 7 (single letter code) | CapF64-X | NSSVGACRSSTMSCARWWCARAYGTN |
| SEQ ID NO: 8 | CapF64 | GCCGACAGGTACCAAAACAAATGT |
| SEQ ID NO: 9 | CapF201-X | (A/G/C/T/absent)(C/A)(C/T)G G(C/A)(G/A)(T/C)GT(C/G)A (G/A)(A/T)AT(C/T)T(C/G)AA (C/T)C(A/G/C/T/absent) |
| SEQ ID NO: 9 (single letter code) | CapF201- | NMYGGMRYGTSARWATYTSAAYCN |
| SEQ ID NO: 10 | CapF201 | CCGGCGTGTCAGAATCTCAACC |
| SEQ ID NO: 11 | AV2cas-X | (A/G/C/T/absent)AC(A/G)(C/ G/T)(A/G)AGANCCAAAGTTCAACTG A(A/C)ACGA(A/G/ C/T/absent) |
| SEQ ID NO: 11 (single letter code) | AV2cas-X | NACRBRAGANCCAAAGTTCAACTGAMA CGAN |
| SEQ ID NO: 12 | AV2cas | ACAGGAGACCAAAGTTCAACTGAAACG A |

In some embodiments, the PCR methods of the invention comprise a first primer having the sequence as set forth in SEQ ID NO: 1 and a second primer having a sequence as set forth in SEQ ID NO: 2. In some embodiments, the PCR methods of the invention comprise a first primer having the sequence as set forth in SEQ ID NO: 3 and a second primer having a sequence as set forth in SEQ ID NO: 4.

The target sequence obtained in the PCR reaction may be all or a portion of the cDNA. In some cases the cDNA is about 50, about 100, about 250, about 500, about 1000, about 2000, about 4000 base pairs in length. In certain cases, the cDNA is approximately 2300 base pairs, approximately 2600 base pairs, or approximately 4700 base pairs in length. However, the invention is not so limited and the actual cDNA length will depend on a variety of factors such as AAV serotype, RT reaction primers, RT reaction condition. In most cases, the cDNA has a length that is sufficient to obtain unique sequence information that can be used to identify the AAV serotype from which the amplified sequences originate.

The target sequence obtained in the PCR reaction may be all or a portion of one or more AAV rep or cap genes, such as VP1, VP2 and VP3. Alternatively, the target sequence obtained in the PCR reaction may be all or a portion of one or more AAV hypervariable regions. In the cases where a portion of a gene (e.g., VP1, VP2, or VP3) is obtained it is understood that the portion will be of a sufficient size and from an appropriate position within the gene (e.g., coding region, variable region) to provide unique sequence information that can be used to identify the AAV serotype from which the amplified sequences originate.

The PCR primers are generated using techniques known to those of skill in the art. Each of the PCR primer sets is composed of a forward primer (i.e., 5' primer) and a reverse primer (i.e., 3' primer). See, e.g., Sambrook J et al. 2000. Molecular Cloning: A Laboratory Manual (Third Edition). The term "primer" refers to an oligonucleotide which provides as a point of initiation of synthesis when placed under conditions (PCR reaction) in which synthesis of a primer extension product which is complementary to a nucleic acid strand is induced. The primer is preferably single stranded. However, if a double stranded primer is utilized, it is treated to separate its strands before being used to prepare extension products. The primers may be about 15 to 30 or more nucleotides, and preferably at least 18 nucleotides. However, for certain applications shorter nucleotides, e.g., 7 to 15 nucleotides are utilized. In certain embodiments, the primers are about 25 nucleotides long (e.g., SEQ ID NO 3 or 4)

The primers are selected to be sufficiently complementary to the different strands of each specific sequence to be amplified such that they hybridize with their respective strands. Typically, hybridization occurs under standard PCR conditions known in the art. Thus, primers having melting temperatures between 50 and 65° C. are normally suitable. However, the invention is not so limited. In addition, the primer sequence need not reflect the exact sequence of the region being amplified. For example, a non-complementary nucleotide fragment may be attached to the 5' end of the primer (e.g., for cloning purposes), with the remainder of the primer sequence being substantially (e.g., completely) complementary to the strand. In some cases, a primer may include a sequence (e.g., 5' sequence) that is not substantially complementary to the target sequence but that facilitates subsequent manipulation of the amplicon (e.g., cDNA). For example, in some cases, a primer may have additional sequence at its 5' end having a unique restriction site that facilitates subsequent digestion by an appropriate restriction enzyme. Methods such as this can be employed to accomplish, for example, a cloning step. Alternatively, non-complementary bases or longer sequences can be interspersed into the primer, provided that the primer sequence has sufficient complementarity with the sequence of the strand to be amplified to hybridize therewith and form a template for synthesis of the extension product of the other primer. Techniques such as these and others disclosed herein are well known in the art and are suitable for use in the methods of the instant invention.

The PCR primers for amplifying the target sequence according to the invention are based upon the highly conserved sequences of two or more aligned sequences (e.g., two or more AAV serotypes). The primers can accommodate less than exact identity among the two or more aligned AAV serotypes at the 5' end or in the middle. However, the sequences at the 3' end of the primers correspond to a region of two or more aligned AAV serotypes in which there is exact identity over at least five, preferably, over at least nine base pairs, and more preferably, over at least 18 base pairs at the 3' end of the primers. Thus, the 3' end of the primers is composed of sequences with 100% identity to the aligned sequences over at least five nucleotides. However, one can optionally utilize one, two, or more degenerate nucleotides at the 3' end of the primer.

As disclosed herein, both rep and cap gene transcripts are detected with variable abundances by RNA detection methods (e.g., RT-PCR). The expression of cap gene transcripts and ability to generate cDNA of cap RNA through reverse transcription (RT) using the methods disclosed herein, significantly increase abundance of templates for PCR-based rescue of novel cap sequences from tissues. The methods of the invention in certain aspects, are useful for isolating novel full length functional cap cDNA sequences. The methods involve the design and selection of oligonucleotide primers for both RT and PCR reactions. As discussed herein, AAV cap gene transcription is directed by AAV p40 promoter which is located in the coding sequence of rep genes. Thus, in some cases, the region between the beginning of p40 RNA transcript and the start codon of capsid VP1 cDNA is a target for the 5' primers to retrieve the intact 5' end of cap cDNA. In order to recover the intact 3' end of the cap transcript, the 3' primer is typically selected in the region of the polyadenylation signal. However, the invention is not so limited and other similar strategies can be employed to isolate novel cDNA sequences of this and other AAV genes.

In some cases, multiple primer sets can be used to isolate novel cDNA sequences of an AAV gene in fragments. Fragments so obtained can, for example, be cloned together to form a single cDNA comprising a complete gene sequence. For example, a first primer set having a 5' primer complementary to an untranslated region of an AAV gene and a 3' primer (anchor primer) complementary to a sequence within the AAV transcript (e.g., in an intronic or exonic sequence) can be used to obtain a first fragment (e.g., a 5' fragment of a gene sequence). A second primer set, having a 5' primer (e.g., anchor primer) complementary to a sequence upstream of the second 3' primer of the first primer set and a 3' primer complementary to a position near the polyadenylation signal can be used to obtain a second fragment (e.g., a 3' fragment of a gene sequence). The two fragments can have any number of uses thereafter, for example they can be analyzed separately (e.g., sequenced) or cloned together to obtain a complete gene sequence. In some cases, three, four, five, six or more primer sets can be used to obtain three, four, five, six or more of AAV gene fragments. Moreover, these examples are not meant to be limiting and any number of primer sets can be employed to obtain any number of fragments provided that the fragments are useful for identifying and obtaining unique AAV sequences (e.g., Capsid gene sequences).

In some cases, the methods involve transfecting cells with total cellular DNAs isolated from the tissues that potentially harbor proviral AAV genomes at very low abundance and supplementing with helper virus function (e.g., adenovirus) to trigger and/or boost AAV rep and cap gene transcription in the transfected cell. In some cases, RNA from the transfected cells provides a template for RT-PCR amplification of cDNA and the detection of novel AAVs. In cases where cells are transfected with total cellular DNAs isolated from the tissues that potentially harbor proviral AAV genomes, it is often desirable to supplement the cells with factors that promote AAV gene transcription. For example, the cells may also be infected with a helper virus, such as an Adenovirus or a Herpes Virus. In a specific embodiment, the helper functions are provided by an adenovirus. The adenovirus may be a wild-type adenovirus, and may be of human or non-human origin, preferably non-human primate (NHP) origin. Similarly adenoviruses known to infect non-human animals (e.g., chimpanzees, mouse) may also be employed in the methods of the invention (See, e.g., U.S. Pat. No. 6,083,716). In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. Nos. 5,871,982 and 6,251,677, which describe a hybrid Ad/AAV virus. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

Cells may also be transfected with a vector (e.g., helper vector) which provides helper functions to the AAV. The vector providing helper functions may provide adenovirus functions, including, e.g., E1a, E1b, E2a, E4ORF6. The sequences of adenovirus gene providing these functions may be obtained from any known adenovirus serotype, such as serotypes 2, 3, 4, 7, 12 and 40, and further including any of the presently identified human types known in the art. Thus, in some embodiments, the methods involve transfecting the cell with a vector expressing one or more genes necessary for AAV replication, AAV gene transcription, and/or AAV packaging.

In some cases, a novel isolated capsid gene can be used to construct and package recombinant AAV vectors, using methods well known in the art, to determine functional characteristics associated with the novel capsid protein encoded by the gene. For example, novel isolated capsid genes can be used to construct and package recombinant AAV (rAAV) vectors comprising a reporter gene (e.g., B-Galactosidase, GFP, Luciferase, etc.). The rAAV vector can then be delivered to an animal (e.g., mouse) and the tissue targeting properties of the novel isolated capsid gene can be determined by examining the expression of the reporter gene in various tissues (e.g., heart, liver, kidneys) of the animal. Other methods for characterizing the novel isolated capsid genes are disclosed herein and still others are well known in the art.

The invention also involves the production of somatic transgenic animal models of disease using recombinant Adeno-Associated Virus (rAAV) based methods. A somatic transgenic animal model is a non-human animal. The methods are based, at least in part, on the observation that AAV serotypes mediate efficient and stable gene transfer in a tissue specific manner in adult animals. The rAAV elements (capsid, promoter, transgene products) are combined to achieve somatic transgenic animal models that express a stable transgene in a time and tissue specific manner. The somatic transgenic animal produced by the methods of the invention can serve as useful models of human disease, pathological state, and/or to characterize the effects of gene for which the function (e.g., tissue specific, disease role) is unknown or not fully understood. For example, an animal (e.g., mouse) can be infected at a distinct developmental stage (e.g., age) with a rAAV comprising a capsid having a specific tissue targeting capability (e.g., liver, heart, pancreas) and a transgene having a tissue specific promoter driving expression of a gene involved in disease. Upon infection, the rAAV infects distinct cells of the target tissue and produces the product of the transgene.

In some embodiments, the transgene causes a pathological state. A transgene that causes a pathological state is a gene whose product has a role in a disease or disorder (e.g., causes the disease or disorder, makes the animal susceptible to the disease or disorder) and/or may induce the disease or disorder in the animal. The animal can then be observed to evaluate any number of aspects of the disease (e.g., progression, response to treatment, etc). These examples are not meant to be limiting, other aspects and examples are disclosed herein and described in more detail below.

The rAAVs useful in the methods of the invention may be those unique rAAVs identified using the methods described herein or may be existing rAAVs known in the art. The rAAVs preferably have tissue-specific targeting capabilities, such that the transgene will be delivered specifically to a predetermined tissue(s). The AAV capsid is an important element in determining these tissue-specific targeting capabilities. Thus an rAAV having a capsid appropriate for the tissue being targeted can be selected.

Methods for obtaining rAAVs having a desired capsid protein are well known in the art. (See, for example, US 2003/0138772), the contents of which are incorporate herein by reference in their entirety). Typically the methods involve culturing a host cell which contains a nucleic acid sequence encoding an AAV capsid protein (e.g., AAV2, AAV5, AAV9) or fragment thereof, as defined herein; a functional rep gene; a recombinant AAV vector composed of, at a minimum, AAV inverted terminal repeats (ITRs) and a transgene; and sufficient helper functions to permit packaging of the recombinant AAV vector into the AAV capsid proteins.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV of the invention may be delivered to the packaging host cell in the form of any genetic element which transfers the sequences publicly carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, J. Virol., 70:520-532 (1993) and U.S. Pat. No. 5,478,745.

The foregoing methods for packaging recombinant vectors in desired AAV capsids to produce the rAAVs of the invention are not meant to be limiting and other suitable methods will be apparent to the skilled artisan.

The recombinant vector is composed of, at a minimum, a transgene and its regulatory sequences, and 5' and 3' AAV inverted terminal repeats (ITRs). It is this recombinant AAV vector which is packaged into a capsid protein and delivered to a selected host cell.

The AAV sequences employed are preferably the cis-acting 5' and 3' inverted terminal repeat sequences [See, e.g., B. J. Carter, in "Handbook of Parvoviruses", ed., P. Tijsser, CRC Press, pp. 155 168 (1990)]. The ITR sequences are about 145 bp in length. Preferably, substantially the entire sequences encoding the ITRs are used in the molecule, although some degree of minor modification of these sequences is permissible. The ability to modify these ITR sequences is within the skill of the art. [See, e.g., texts such as Sambrook et al, "Molecular Cloning. A Laboratory Manual", 2d ed., Cold Spring Harbor Laboratory, New York (1989); and K. Fisher et al., J. Virol., 70:520 532 (1996)]. An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. For example, the ITRs may be provided by AAV type 1, AAV type 2, AAV type 3, AAV type 4, AAV type 5, AAV 6, other AAV serotypes or parvovirus, e.g., densovirus.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence, miRNA sequence, shRNA sequence, miRNA sponge sequence etc.) and regulatory sequences are said to be "operably" joined when they are covalently linked in such a way as to place the expression or transcription of the nucleic acid sequence under the influence or control of the regulatory sequences. If it is desired that the nucleic acid sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a nucleic acid sequence if the promoter region were capable of effecting transcription of that DNA sequence such that the resulting transcript might be translated into the desired protein or polypeptide. Similarly two or more coding regions are operably joined when they are linked in such a way that their transcription from a common promoter results in the expression of two or more proteins having been translated in frame. In some embodiments, operably joined coding sequences yield a fusion protein.

The polyadenylation sequence generally is inserted following the transgene sequences and before the 3' AAV ITR sequence. A rAAV construct useful in the present invention may also contain an intron, desirably located between the promoter/enhancer sequence and the transgene. One possible intron sequence is also derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989].

The target sites in the mRNA may be in the 5' UTR, the 3' UTR or in the coding region. Interestingly, multiple miRNAs may regulate the same mRNA target by recognizing the same or multiple sites. The nucleic acid may also comprise a sequence of a target miRNA binding site, or a variant thereof. The presence of multiple miRNA binding sites in most genetically identified targets may indicate that the cooperative action of multiple RISCs provides the most efficient translational inhibition. The target site sequence may comprise a total of 5-100 or 10-60 nucleotides. The target site sequence may comprise at least 5 nucleotides of the sequence of a target gene binding site.

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, Proc. Natl. Acad. Sci. USA, 93:3346-3351 (1996)], the tetracycline-repressible system [Gossen et al, Proc. Natl. Acad. Sci. USA, 89:5547-5551 (1992)], the tetracycline-inducible system [Gossen et al, Science, 268:1766-1769 (1995), see also Harvey et al, Curr. Opin. Chem. Biol., 2:512-518 (1998)], the RU486-inducible system [Wang et al, Nat. Biotech., 15:239-243 (1997) and Wang et al, Gene Ther., 4:432-441 (1997)] and the rapamycin-inducible system [Magari et al, J. Clin. Invest., 100:2865-2872 (1997)]. Still other types of inducible promoters which may be useful in this context are those which are regulated by a specific physiological state, e.g., temperature, acute phase, a particular differentiation state of the cell, or in replicating cells only.

Genes encoding small interfering nucleic acids, e.g., miRNAs, miRNA Inhibitors, may be expressed from any appropriate promoter, including, but not limited to, a RNA polymerase II promoter, a RNA polymerase III promoter, or a combination thereof. A small interfering nucleic acid, e.g., miRNA, miRNA Inhibitor, may be operably joined with a combination of promoters including, for example, a combination of a RNA polymerase II promoter and a RNA III promoter.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In preferred embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, a insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, the transgene is a nucleic acid sequence, heterologous to the vector sequences, which encodes a polypeptide, protein, RNA molecule (e.g., miRNA, miRNA sponge) or other gene product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer. Such reporters can, for example, be useful in verifying the tissue-specific targeting capabilities and tissue specific promoter regulatory activity of an rAAV.

The invention in some aspects, provide methods for producing somatic transgenic animal models through the targeted destruction of specific cell types. For example, models of type 1 diabetes can be produced by the targeted destruction of pancreatic Beta-islets. In other examples, the targeted destruction of specific cell types can be used to evaluate the role of specific cell types on human disease. In this regard, transgenes that encode cellular toxins (e.g., diphtheria toxin A (DTA)) or pro-apoptotic genes (NTR, Box, etc.) can be useful as transgenes for functional ablation of specific cell types. Other exemplary transgenes, whose products kill cells are embraced by the methods disclosed herein and will be apparent to one of ordinary skill in the art.

The long term over expression or knockdown (e.g., by miRNA and/or miRNA sponge) of genes in specific target tissues can disturb normal metabolic balance and establish a pathological state, thereby producing an animal model of diseases such as cancer. The invention in some aspects, provides methods for producing somatic transgenic animal models to study the long-term effects of over-expression or knockdown of potential oncogenes and other genes to study tumorigenesis and gene function in the targeted tissues. Useful transgene products include proteins that are known to be associated with cancer and small interfering nucleic acids inhibiting the expression of such proteins. The following is a non-limiting list of gene known to be associated with the development of cancer (e.g., oncogenes and tumor suppressors) and nucleic acids encoding the products of these genes and their homologues and encoding small interfering nucleic acids (e.g., shRNAs, miRNAs, miRNA sponges) that inhibit the expression of these genes and their homologues are useful as transgenes in certain embodiments of the methods: AARS, ABCB1, ABCC4, ABI2, ABL1, ABL2, ACK1, ACP2, ACY1, ADSL, AK1, AKR1C2, AKT1, ALB, ANPEP, ANXA5, ANXA7, AP2M1, APC, ARHGAP5, ARHGEF5, ARID4A, ASNS, ATF4, ATM, ATP5B, ATP5O, AXL, BARD1, BAX, BCL2, BHLHB2, BLMH, BRAF, BRCA1, BRCA2, BTK, CANX, CAP1, CAPN1, CAPNS1, CAV1, CBFB, CBLB, CCL2, CCND1, CCND2, CCND3, CCNE1, CCT5, CCYR61, CD24, CD44, CD59, CDC20, CDC25, CDC25A, CDC25B, CDC2L5, CDK10, CDK4, CDK5, CDK9, CDKL1, CDKN1A, CDKN1B, CDKN1C, CDKN2A, CDKN2B, CDKN2D, CEBPG, CENPC1, CGRRF1, CHAF1A, CIB1, CKMT1, CLK1, CLK2, CLK3, CLNS1A, CLTC, COL1A1, COL6A3, COX6C, COX7A2, CRAT, CRHR1, CSF1R, CSK, CSNK1G2, CTNNA1, CTNNB1, CTPS, CTSC, CTSD, CUL1, CYR61, DCC, DCN, DDX10, DEK, DHCR7, DHRS2, DHX8, DLG3, DVL1, DVL3, E2F1, E2F3, E2F5, EGFR, EGR1, EIF5, EPHA2, ERBB2, ERBB3, ERBB4, ERCC3, ETV1, ETV3, ETV6, F2R, FASTK, FBN1, FBN2, FES, FGFR1, FGR, FKBP8, FN1, FOS, FOSL1, FOSL2, FOXG1A, FOXO1A, FRAP1, FRZB, FTL, FZD2, FZD5, FZD9, G22P1, GAS6, GCN5L2, GDF15, GNA13, GNAS, GNB2, GNB2L1, GPR39, GRB2, GSK3A, GSPT1, GTF2I, HDAC1, HDGF, HMMR, HPRT1, HRB, HSPA4, HSPA5, HSPA8, HSPB1, HSPH1, HYAL1, HYOU1, ICAM1, ID1, ID2, IDUA, IER3, IFITM1, IGF1R, IGF2R, IGFBP3, IGFBP4, IGFBP5, IL1B, ILK, ING1, IRF3, ITGA3, ITGA6, ITGB4, JAK1, JARID1A, JUN, JUNB, JUND, K-ALPHA-1, KIT, KITLG, KLK10, KPNA2, KRAS2, KRT18, KRT2A, KRT9, LAMB1, LAMP2, LCK, LCN2, LEP, LITAF, LRPAP1, LTF, LYN, LZTR1, MADH1, MAP2K2, MAP3K8, MAPK12, MAPK13, MAPKAPK3, MAPRE1, MARS, MAS1, MCC, MCM2, MCM4, MDM2, MDM4, MET, MGST1, MICB, MLLT3, MME, MMP1, MMP14, MMP17, MMP2, MNDA, MSH2, MSH6, MT3, MYB, MYBL1, MYBL2, MYC, MYCL1, MYCN, MYD88, MYL9, MYLK, NEO1, NF1, NF2, NFKB1, NFKB2, NFSF7, NID, NINJ1, NMBR, NME1, NME2, NME3, NOTCH1, NOTCH2, NOTCH4, NPM1, NQO1, NR1D1, NR2F1, NR2F6, NRAS, NRG1, NSEP1, OSM, PA2G4, PABPC1, PCNA, PCTK1, PCTK2, PCTK3, PDGFA, PDGFB, PDGFRA, PDPK1, PEA15, PFDN4, PFDN5, PGAM1, PHB, PIK3CA, PIK3CB, PIK3CG, PIM1, PKM2, PKMYT1, PLK2, PPARD, PPARG, PPIH, PPP1CA, PPP2R5A, PRDX2, PRDX4, PRKAR1A, PRKCBP1, PRNP, PRSS15, PSMA1, PTCH, PTEN, PTGS1, PTMA, PTN, PTPRN, RAB5A, RAC1, RAD50, RAF1, RALBP1, RAP1A, RARA, RARB, RASGRF1, RB1, RBBP4, RBL2, REA, REL, RELA, RELB, RET, RFC2, RGS19, RHOA, RHOB, RHOC, RHOD, RIPK1, RPN2, RPS6 KB1, RRM1, SARS, SELENBP1, SEMA3C, SEMA4D, SEPP1, SERPINH1, SFN, SFPQ, SFRS7, SHB, SHH, SIAH2, SIVA, SIVA TP53, SKI, SKIL, SLC16A1, SLC1A4, SLC20A1, SMO, SMPD1, SNAI2, SND1, SNRPB2, SOCS1, SOCS3, SOD1, SORT1, SPINT2, SPRY2, SRC, SRPX, STAT1, STAT2, STAT3, STAT5B, STC1, TAF1, TBL3, TBRG4, TCF1, TCF7L2, TFAP2C, TFDP1, TFDP2, TGFα, TGFB1, TGFBI, TGFBR2, TGFBR3, THBS1, TIE, TIMP1, TIMP3, TJP1, TK1, TLE1, TNF, TNFRSF10A, INFRSF10B, TNFRSF1A, TNFRSF1B, TNFRSF6, TNFSF7, TNK1, TOB1, TP53, TP53BP2, TP5313, TP73, TPBG, TPT1, TRADD, TRAM1, TRRAP, TSG101, TUFM, TXNRD1, TYRO3, UBC, UBE2L6, UCHL1, USP7, VDAC1, VEGF, VHL, VIL2, WEE1, WNT1, WNT2, WNT2B, WNT3, WNT5A, WT1, XRCC1, YES1, YWHAB, YWHAZ, ZAP70, and ZNF9.

Other useful transgene products include proteins that are known to be associated with apoptosis. The following is a non-limiting list of gene known to be associated with apoptosis and nucleic acids encoding the products of these genes and their homologues and encoding small interfering nucleic acids (e.g., shRNAs, miRNAs, miRNA sponges) that inhibit the expression of these genes and their homologues are useful as transgenes in certain embodiments of the methods: RPS27A, ABL1, AKT1, APAF1, BAD, BAG1, BAG3, BAG4, BAK1, BAX, BCL10, BCL2, BCL2A1, BCL2L1, BCL2L10, BCL2L11, BCL2L12, BCL2L13, BCL2L2, BCLAF1, BFAR, BID, BIK, NAIP, BIRC2, BIRC3, XIAP, BIRC5, BIRC6, BIRC7, BIRC8, BNIP1, BNIP2, BNIP3, BNIP3L, BOK, BRAF, CARD10, CARD11, NLRC4, CARD14, NOD2, NOD1, CARD6, CARD8, CARD9, CASP1, CASP10, CASP14, CASP2, CASP3, CASP4, CASP5, CASP6, CASP7, CASP8, CASP9, CFLAR, CIDEA, CIDEB, CRADD, DAPK1, DAPK2, DFFA, DFFB, FADD, GADD45A, GDNF, HRK, IGF1R, LTA, LTBR, MCL1, NOL3, PYCARD, RIPK1, RIPK2, TNF, TNFRSF10A, TNFRSF10B, TNFRSF10C, TNFRSF10D, TNFRSF11B, TNFRSF12A, TNFRSF14, TNFRSF19, TNFRSF1A, TNFRSF1B, TNFRSF21, TNFRSF25, CD40, FAS, TNFRSF6B, CD27, TNFRSF9, TNFSF10, TNFSF14, TNFSF18, CD40LG, FASLG, CD70, TNFSF8, TNFSF9, TP53, TP53BP2, TP73, TP63, TRADD, TRAF1, TRAF2, TRAF3, TRAF4, and TRAF5.

In some embodiments, the sequence of the coding region of a transgene is modified. In some cases, the modification alters the function of the product encoded by the transgene. The effect of the modification can then be studied in vivo by generating a somatic transgenic animal model using the methods disclosed herein. In some embodiments, modification of the sequence of coding region is a nonsense mutation that results in a fragment (e.g., a truncated version). In other cases, the modification is a missense mutation that results in an amino acid substitution. Other modifications are possible and will be apparent to the skilled artisan.

The skilled artisan will also realize that in the case of transgenes encoding proteins or polypeptides, that conservative amino acid substitutions may be made in transgenes to provide functionally equivalent variants, or homologs of the proteins or polypeptides. In some aspects the invention embraces sequence alterations that result in conservative amino acid substitution of a transgene. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

miRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into an miRNA duplex, and further into a "mature" single stranded miRNA molecule. This mature miRNA guides a multiprotein complex, miRISC, which identifies target 3' UTR regions of target mRNAs based upon their complementarity to the mature miRNA. The invention in some aspects relates to the study of microRNA function in specific target tissues and cell types. Thus, useful transgene products include miRNAs. The following is a non-limiting list of miRNA genes; the products of these genes and their homologues are useful as transgenes or as targets for small interfering nucleic acids (e.g., miRNA sponges, antisense oligonucleotides) in certain embodiments of the methods: hsa-let-7a, hsa-let-7a*, hsa-let-7b, hsa-let-7b*, hsa-let-7c, hsa-let-7c*, hsa-let-7d, hsa-let-7d*, hsa-let-7e, hsa-let-7e*, hsa-let-7f, hsa-let-7f-1*, hsa-let-7f-2*, hsa-let-7g, hsa-let-7g*, hsa-let-7i, hsa-let-7i*, hsa-miR-1, hsa-miR-100, hsa-miR-100*, hsa-miR-101, hsa-miR-101*, hsa-miR-103, hsa-miR-105, hsa-miR-105*, hsa-miR-106a, hsa-miR-106a*, hsa-miR-106b, hsa-miR-106b*, hsa-miR-107, hsa-miR-10a, hsa-miR-10a*, hsa-miR-10b, hsa-miR-10b*, hsa-miR-1178, hsa-miR-1179, hsa-miR-1180, hsa-miR-1181, hsa-miR-1182, hsa-miR-1183, hsa-miR-1184, hsa-miR-1185, hsa-miR-1197, hsa-miR-1200, hsa-miR-1201, hsa-miR-1202, hsa-miR-1203, hsa-miR-1204, hsa-miR-1205, hsa-miR-1206, hsa-miR-1207-3p, hsa-miR-1207-5p, hsa-miR-1208, hsa-miR-122, hsa-miR-122*, hsa-miR-1224-3p, hsa-miR-1224-5p, hsa-miR-1225-3p, hsa-miR-1225-5p, hsa-miR-1226, hsa-miR-1226*, hsa-miR-1227, hsa-miR-1228, hsa-miR-1228*, hsa-miR-1229, hsa-miR-1231, hsa-miR-1233, hsa-miR-1234, hsa-miR-1236, hsa-miR-1237, hsa-miR-1238, hsa-miR-124, hsa-miR-124*, hsa-miR-1243, hsa-miR-1244, hsa-miR-1245, hsa-miR-1246, hsa-miR-1247, hsa-miR-1248, hsa-miR-1249, hsa-miR-1250, hsa-miR-1251, hsa-miR-1252, hsa-miR-1253, hsa-miR-1254, hsa-miR-1255a, hsa-miR-1255b, hsa-miR-1256, hsa-miR-1257, hsa-miR-1258, hsa-miR-1259, hsa-miR-125a-3p, hsa-miR-125a-5p, hsa-miR-125b, hsa-miR-125b-1*, hsa-miR-125b-2*, hsa-miR-126, hsa-miR-126*, hsa-miR-1260, hsa-miR-1261, hsa-miR-1262, hsa-miR-1263, hsa-miR-1264, hsa-miR-1265, hsa-miR-1266, hsa-miR-1267, hsa-miR-1268, hsa-miR-1269, hsa-miR-1270, hsa-miR-1271, hsa-miR-1272, hsa-miR-1273, hsa-miR-127-3p, hsa-miR-1274a, hsa-miR-1274b, hsa-miR-1275, hsa-miR-127-5p, hsa-miR-1276, hsa-miR-1277, hsa-miR-1278, hsa-miR-1279, hsa-miR-128, hsa-miR-1280, hsa-miR-1281, hsa-miR-1282, hsa-miR-1283, hsa-miR-1284, hsa-miR-1285, hsa-miR-1286, hsa-miR-1287, hsa-miR-1288, hsa-miR-1289, hsa-miR-129*, hsa-miR-1290, hsa-miR-1291, hsa-miR-1292, hsa-miR-1293, hsa-miR-129-3p, hsa-miR-1294, hsa-miR-1295, hsa-miR-129-5p, hsa-miR-1296, hsa-miR-1297, hsa-miR-1298, hsa-miR-1299, hsa-miR-1300, hsa-miR-1301, hsa-miR-1302, hsa-miR-1303, hsa-miR-1304, hsa-miR-1305, hsa-miR-1306, hsa-miR-1307, hsa-miR-1308, hsa-miR-130a, hsa-miR-130a*, hsa-miR-130b, hsa-miR-130b*, hsa-miR-132, hsa-miR-132*, hsa-miR-1321, hsa-miR-1322, hsa-miR-1323, hsa-miR-1324, hsa-miR-133a, hsa-miR-133b, hsa-miR-134, hsa-miR-135a, hsa-miR-135a*, hsa-miR-135b, hsa-miR-135b*, hsa-miR-136, hsa-miR-136*, hsa-miR-137, hsa-miR-138, hsa-miR-138-1*, hsa-miR-138-2*, hsa-miR-139-3p, hsa-miR-139-5p, hsa-miR-140-3p, hsa-miR-140-5p, hsa-miR-141, hsa-miR-141*, hsa-miR-142-3p, hsa-miR-142-5p, hsa-miR-143, hsa-miR-143*, hsa-miR-144, hsa-miR-144*, hsa-miR-145, hsa-miR-145*, hsa-miR-146a, hsa-miR-146a*, hsa-miR-146b-3p, hsa-miR-146b-5p, hsa-miR-147, hsa-miR-147b, hsa-miR-148a, hsa-miR-148a*, hsa-miR-148b, hsa-miR-148b*, hsa-miR-149, hsa-miR-149*, hsa-miR-150, hsa-miR-150*, hsa-miR-151-3p, hsa-miR-151-5p, hsa-miR-152, hsa-miR-153, hsa-miR-154, hsa-miR-154*, hsa-miR-155, hsa-miR-155*, hsa-miR-15a, hsa-miR-15a*, hsa-miR-15b, hsa-miR-15b*, hsa-miR-16, hsa-miR-16-1*, hsa-miR-16-2*, hsa-miR-17, hsa-miR-17*, hsa-miR-181a, hsa-miR-181a*, hsa-miR-181a-2*, hsa-miR-181b, hsa-miR-181c, hsa-miR-181c*, hsa-miR-181d, hsa-miR-182, hsa-miR-182*, hsa-miR-1825, hsa-miR-1826, hsa-miR-1827, hsa-miR-183, hsa-miR-183*, hsa-miR-184, hsa-miR-185, hsa-miR-185*, hsa-miR-186, hsa-miR-186*, hsa-miR-187, hsa-miR-187*, hsa-miR-188-3p, hsa-miR-188-5p, hsa-miR-18a, hsa-miR-18a*, hsa-miR-18b, hsa-miR-18b*, hsa-miR-190, hsa-miR-190b, hsa-miR-191, hsa-miR-191*, hsa-miR-192, hsa-miR-192*, hsa-miR-193a-3p, hsa-miR-193a-5p, hsa-miR-193b, hsa-miR-193b*, hsa-miR-194, hsa-miR-194*, hsa-miR-195, hsa-miR-195*, hsa-miR-196a, hsa-miR-196a*, hsa-miR-196b, hsa-miR-197, hsa-miR-198, hsa-miR-199a-3p, hsa-miR-199a-5p, hsa-miR-199b-5p, hsa-miR-19a, hsa-miR-19a*, hsa-miR-19b, hsa-miR-19b-1*, hsa-miR-19b-2*, hsa-miR-200a, hsa-miR-200a*, hsa-miR-200b, hsa-miR-200b*, hsa-miR-200c, hsa-miR-200c*, hsa-miR-202, hsa-miR-202*, hsa-miR-203, hsa-miR-204, hsa-miR-205, hsa-miR-206, hsa-miR-208a, hsa-miR-208b, hsa-miR-20a, hsa-miR-20a*, hsa-miR-20b, hsa-miR-20b*, hsa-miR-21, hsa-miR-21*, hsa-miR-210, hsa-miR-211, hsa-miR-212, hsa-miR-214, hsa-miR-214*, hsa-miR-215, hsa-miR-216a, hsa-miR-216b, hsa-miR-217, hsa-miR-218, hsa-miR-218-1*, hsa-miR-218-2*, hsa-miR-219-1-3p, hsa-miR-219-2-3p, hsa-miR-219-5p, hsa-miR-22, hsa-miR-22*, hsa-miR-220a, hsa-miR-220b, hsa-miR-220c, hsa-miR-221, hsa-miR-221*, hsa-miR-222, hsa-miR-222*, hsa-miR-223, hsa-miR-223*, hsa-miR-224, hsa-miR-23a, hsa-miR-23a*, hsa-miR-23b, hsa-miR-23b*, hsa-miR-24, hsa-miR-24-1*, hsa-miR-24-2*, hsa-miR-25, hsa-miR-25*, hsa-miR-26a, hsa-miR-26a-1*, hsa-miR-26a-2*, hsa-miR-26b, hsa-miR-26b*, hsa-miR-27a, hsa-miR-27a*, hsa-miR-27b, hsa-miR-27b*, hsa-miR-28-3p, hsa-miR-28-5p, hsa-miR-296-3p, hsa-miR-296-5p, hsa-miR-297, hsa-miR-298, hsa-miR-299-3p, hsa-miR-299-5p, hsa-miR-29a, hsa-miR-29a*, hsa-miR-29b, hsa-miR-29b-1*, hsa-miR-29b-2*, hsa-miR-29c, hsa-miR-29c*, hsa-miR-300, hsa-miR-301a, hsa-miR-301b, hsa-miR-302a, hsa-miR-302a*, hsa-miR-302b, hsa-miR-302b*, hsa-miR-302c, hsa-miR-302c*, hsa-miR-302d, hsa-miR-302d*, hsa-miR-302e, hsa-miR-302f, hsa-miR-30a, hsa-miR-30a*, hsa-miR-30b, hsa-miR-30b*, hsa-miR-30c, hsa-miR-30c-1*, hsa-miR-30c-2*, hsa-miR-30d, hsa-miR-30d*, hsa-miR-30e, hsa-miR-30e*, hsa-miR-31, hsa-miR-31*, hsa-miR-32, hsa-miR-32*, hsa-miR-320a, hsa-miR-320b, hsa-miR-320c, hsa-miR-320d, hsa-miR-323-3p, hsa-miR-323-5p, hsa-miR-324-3p, hsa-miR-324-5p, hsa-miR-325, hsa-miR-326, hsa-miR-328, hsa-miR-329, hsa-miR-330-3p, hsa-miR-330-5p, hsa-miR-331-3p, hsa-miR-331-5p, hsa-miR-335, hsa-miR-335*, hsa-miR-337-3p, hsa-miR-337-5p, hsa-miR-338-3p, hsa-miR-338-5p, hsa-miR-339-3p, hsa-miR-339-5p, hsa-miR-33a, hsa-miR-33a*, hsa-miR-33b, hsa-miR-33b*, hsa-miR-340, hsa-miR-340*, hsa-miR-342-3p, hsa-miR-342-5p, hsa-miR-345, hsa-miR-346, hsa-miR-34a, hsa-miR-34a*, hsa-miR-34b, hsa-miR-34b*, hsa-miR-34c-3p, hsa-miR-34c-5p, hsa-miR-361-3p, hsa-miR-361-5p, hsa-miR-362-3p, hsa-miR-362-5p, hsa-miR-363, hsa-miR-363*, hsa-miR- 365, hsa-miR-367, hsa-miR-367*, hsa-miR-369-3p, hsa-miR-369-5p, hsa-miR-370, hsa-miR-371-3p, hsa-miR-371-5p, hsa-miR-372, hsa-miR-373, hsa-miR-373*, hsa-miR-374a, hsa-miR-374a*, hsa-miR-374b, hsa-miR-374b*, hsa-miR-375, hsa-miR-376a, hsa-miR-376a*, hsa-miR-376b, hsa-miR-376c, hsa-miR-377, hsa-miR-377*, hsa-miR-378, hsa-miR-378*, hsa-miR-379, hsa-miR-379*, hsa-miR-380, hsa-miR-380*, hsa-miR-381, hsa-miR-382, hsa-miR-383, hsa-miR-384, hsa-miR-409-3p, hsa-miR-409-5p, hsa-miR-410, hsa-miR-411, hsa-miR-411*, hsa-miR-412, hsa-miR-421, hsa-miR-422a, hsa-miR-423-3p, hsa-miR-423-5p, hsa-miR-424, hsa-miR-424*, hsa-miR-425, hsa-miR-425*, hsa-miR-429, hsa-miR-431, hsa-miR-431*, hsa-miR-432, hsa-miR-432*, hsa-miR-433, hsa-miR-448, hsa-miR-449a, hsa-miR-449b, hsa-miR-450a, hsa-miR-450b-3p, hsa-miR-450b-5p, hsa-miR-451, hsa-miR-452, hsa-miR-452*, hsa-miR-453, hsa-miR-454, hsa-miR-454*, hsa-miR-455-3p, hsa-miR-455-5p, hsa-miR-483-3p, hsa-miR-483-5p, hsa-miR-484, hsa-miR-485-3p, hsa-miR-485-5p, hsa-miR-486-3p, hsa-miR-486-5p, hsa-miR-487a, hsa-miR-487b, hsa-miR-488, hsa-miR-488*, hsa-miR-489, hsa-miR-490-3p, hsa-miR-490-5p, hsa-miR-491-3p, hsa-miR-491-5p, hsa-miR-492, hsa-miR-493, hsa-miR-493*, hsa-miR-494, hsa-miR-495, hsa-miR-496, hsa-miR-497, hsa-miR-497*, hsa-miR-498, hsa-miR-499-3p, hsa-miR-499-5p, hsa-miR-500, hsa-miR-500*, hsa-miR-501-3p, hsa-miR-501-5p, hsa-miR-502-3p, hsa-miR-502-5p, hsa-miR-503, hsa-miR-504, hsa-miR-505, hsa-miR-505*, hsa-miR-506, hsa-miR-507, hsa-miR-508-3p, hsa-miR-508-5p, hsa-miR-509-3-5p, hsa-miR-509-3p, hsa-miR-509-5p, hsa-miR-510, hsa-miR-511, hsa-miR-512-3p, hsa-miR-512-5p, hsa-miR-513a-3p, hsa-miR-513a-5p, hsa-miR-513b, hsa-miR-513c, hsa-miR-514, hsa-miR-515-3p, hsa-miR-515-5p, hsa-miR-516a-3p, hsa-miR-516a-5p, hsa-miR-516b, hsa-miR-517*, hsa-miR-517a, hsa-miR-517b, hsa-miR-517c, hsa-miR-518a-3p, hsa-miR-518a-5p, hsa-miR-518b, hsa-miR-518c, hsa-miR-518c*, hsa-miR-518d-3p, hsa-miR-518d-5p, hsa-miR-518e, hsa-miR-518e*, hsa-miR-518f, hsa-miR-518f*, hsa-miR-519a, hsa-miR-519b-3p, hsa-miR-519c-3p, hsa-miR-519d, hsa-miR-519e, hsa-miR-519e*, hsa-miR-520a-3p, hsa-miR-520a-5p, hsa-miR-520b, hsa-miR-520c-3p, hsa-miR-520d-3p, hsa-miR-520d-5p, hsa-miR-520e, hsa-miR-520f, hsa-miR-520g, hsa-miR-520h, hsa-miR-521, hsa-miR-522, hsa-miR-523, hsa-miR-524-3p, hsa-miR-524-5p, hsa-miR-525-3p, hsa-miR-525-5p, hsa-miR-526b, hsa-miR-526b*, hsa-miR-532-3p, hsa-miR-532-5p, hsa-miR-539, hsa-miR-541, hsa-miR-541*, hsa-miR-542-3p, hsa-miR-542-5p, hsa-miR-543, hsa-miR-544, hsa-miR-545, hsa-miR-545*, hsa-miR-548a-3p, hsa-miR-548a-5p, hsa-miR-548b-3p, hsa-miR-548b-5p, hsa-miR-548c-3p, hsa-miR-548c-5p, hsa-miR-548d-3p, hsa-miR-548d-5p, hsa-miR-548e, hsa-miR-548f, hsa-miR-548g, hsa-miR-548h, hsa-miR-548i, hsa-miR-548j, hsa-miR-548k, hsa-miR-548l, hsa-miR-548m, hsa-miR-548n, hsa-miR-548o, hsa-miR-548p, hsa-miR-549, hsa-miR-550, hsa-miR-550*, hsa-miR-551a, hsa-miR-551b, hsa-miR-551b*, hsa-miR-552, hsa-miR-553, hsa-miR-554, hsa-miR-555, hsa-miR-556-3p, hsa-miR-556-5p, hsa-miR-557, hsa-miR-558, hsa-miR-559, hsa-miR-561, hsa-miR-562, hsa-miR-563, hsa-miR-564, hsa-miR-566, hsa-miR-567, hsa-miR-568, hsa-miR-569, hsa-miR-570, hsa-miR-571, hsa-miR-572, hsa-miR-573, hsa-miR-574-3p, hsa-miR-574-5p, hsa-miR-575, hsa-miR-576-3p, hsa-miR-576-5p, hsa-miR-577, hsa-miR-578, hsa-miR-579, hsa-miR-580, hsa-miR-581, hsa-miR-582-3p, hsa-miR-582-5p, hsa-miR-583, hsa-miR-584, hsa-miR-585, hsa-miR-586, hsa-miR-587, hsa-miR-588, hsa-miR-589, hsa-miR-589*, hsa-miR-590-3p, hsa-miR-590-5p, hsa-miR-591, hsa-miR-592, hsa-miR-593, hsa-miR-593*, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615-3p, hsa-miR-615-5p, hsa-miR-616, hsa-miR-616*, hsa-miR-617, hsa-miR-618, hsa-miR-619, hsa-miR-620, hsa-miR-621, hsa-miR-622, hsa-miR-623, hsa-miR-624, hsa-miR-624*, hsa-miR-625, hsa-miR-625*, hsa-miR-626, hsa-miR-627, hsa-miR-628-3p, hsa-miR-628-5p, hsa-miR-629, hsa-miR-629*, hsa-miR-630, hsa-miR-631, hsa-miR-632, hsa-miR-633, hsa-miR-634, hsa-miR-635, hsa-miR-636, hsa-miR-637, hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-653, hsa-miR-654-3p, hsa-miR-654-5p, hsa-miR-655, hsa-miR-656, hsa-miR-657, hsa-miR-658, hsa-miR-659, hsa-miR-660, hsa-miR-661, hsa-miR-662, hsa-miR-663, hsa-miR-663b, hsa-miR-664, hsa-miR-664*, hsa-miR-665, hsa-miR-668, hsa-miR-671-3p, hsa-miR-671-5p, hsa-miR-675, hsa-miR-7, hsa-miR-708, hsa-miR-708*, hsa-miR-7-1*, hsa-miR-7-2*, hsa-miR-720, hsa-miR-744, hsa-miR-744*, hsa-miR-758, hsa-miR-760, hsa-miR-765, hsa-miR-766, hsa-miR-767-3p, hsa-miR-767-5p, hsa-miR-768-3p, hsa-miR-768-5p, hsa-miR-769-3p, hsa-miR-769-5p, hsa-miR-770-5p, hsa-miR-802, hsa-miR-873, hsa-miR-874, hsa-miR-875-3p, hsa-miR-875-5p, hsa-miR-876-3p, hsa-miR-876-5p, hsa-miR-877, hsa-miR-877*, hsa-miR-885-3p, hsa-miR-885-5p, hsa-miR-886-3p, hsa-miR-886-5p, hsa-miR-887, hsa-miR-888, hsa-miR-888*, hsa-miR-889, hsa-miR-890, hsa-miR-891a, hsa-miR-891b, hsa-miR-892a, hsa-miR-892b, hsa-miR-9, hsa-miR-9*, hsa-miR-920, hsa-miR-921, hsa-miR-922, hsa-miR-923, hsa-miR-924, hsa-miR-92a, hsa-miR-92a-1*, hsa-miR-92a-2*, hsa-miR-92b, hsa-miR-92b*, hsa-miR-93, hsa-miR-93*, hsa-miR-933, hsa-miR-934, hsa-miR-935, hsa-miR-936, hsa-miR-937, hsa-miR-938, hsa-miR-939, hsa-miR-940, hsa-miR-941, hsa-miR-942, hsa-miR-943, hsa-miR-944, hsa-miR-95, hsa-miR-96, hsa-miR-96*, hsa-miR-98, hsa-miR-99a, hsa-miR-99a*, hsa-miR-99b, and hsa-miR-99b*. In some embodiments, one or more bindings sites for one or more of the foregoing miRNAs are incorporated in a transgene, e.g., a transgene delivered by a rAAV vector, to inhibit the expression of the transgene in one or more tissues of an animal harboring the transgene. The skilled artisan will appreciate that binding sites may be selected to control the expression of a trangene in a tissue specific manner. For example, binding sites for the liver-specific miR-122 may be incorporated into a transgene to inhibit expression of that transgene in the liver.

An miRNA inhibits the function of the mRNAs it targets and, as a result, inhibits expression of the polypeptides encoded by the mRNAs. Thus, blocking (partially or totally) the activity of the miRNA (e.g., silencing the miRNA) can effectively induce, or restore, expression of a polypeptide whose expression is inhibited (derepress the polypeptide). In one embodiment, derepression of polypeptides encoded by mRNA targets of an miRNA is accomplished by inhibiting the miRNA activity in cells through any one of a variety of methods. For example, blocking the activity of an miRNA can be accomplished by hybridization with a small interfering nucleic acid (e.g., antisense oligonucleotide, miRNA sponge) that is complementary, or substantially complementary to, the miRNA, thereby blocking interaction of the miRNA with its target mRNA. As used herein, an small interfering nucleic acid that is substantially complementary to an miRNA is one that is capable of hybridizing with an miRNA, and blocking the miRNA's activity. In some embodiments, an small interfering nucleic acid that is substantially complementary to an miRNA is an small interfering nucleic acid that is complementary with the miRNA at all but 1, 2, 3, 4, 5, 6, 7, 8, 9, 10, 11, 12, 13, 14, 15, 16, 17, or 18 bases. In some embodiments, an small interfering nucleic acid sequence that is substantially complementary to an miRNA, is an small interfering nucleic acid sequence that is complementary with the miRNA at, at least, one base. MicroRNA inhibitors, e.g., miRNA sponges, can be expressed in cells from transgenes (Ebert, M. S. Nature Methods, Epub Aug. 12, 2007). These miRNA sponges specifically inhibit miRNAs through a complementary heptameric seed sequence and an entire family of miRNAs can be silenced using a single sponge sequence. Other transgenic methods for silencing miRNA function (derepression of miRNA targets) in cells will be apparent to one of ordinary skill in the art.

Other suitable transgenes may be readily selected by one of skill in the art provided that they are useful for creating animal models of tissue-specific pathological state and/or disease.

A "miR Inhibitor" or "miRNA Inhibitor" is an agent that blocks miRNA expression and/or processing. For instance, these molecules include but are not limited to microRNA antagonists, microRNA specific antisense, microRNA sponges, and microRNA oligonucleotides (double-stranded, hairpin, short oligonucleotides) that inhibit miRNA interaction with a Drosha complex. MicroRNA inhibitors, e.g., miRNA sponges, can be expressed in cells from transgenes (Ebert, M. S. Nature Methods, Epub Aug. 12, 2007). The invention encompasses the use of microRNA sponges, or other miR Inhibitors, with the AAVs. These microRNA sponges specifically inhibit miRNAs through a complementary heptameric seed sequence. An entire family of miRNAs can be silenced using a single sponge sequence. Other methods for silencing miRNA function (derepression of miRNA targets) in cells will be apparent to one of ordinary skill in the art.

The rAAVs may be delivered to host animal in compositions according to any appropriate methods known in the art. The rAAV, preferably suspended in a physiologically compatible carrier (i.e., in a composition), may be administered to a host animal, such as a mouse, rat, cat, dog, sheep, rabbit, horse, cow, goat, pig, guinea pig, hamster, chicken, turkey, or a non-human primate (e.g, Macaque). In some embodiments a host animal does not include a human.

The compositions of the invention may comprise an rAAV alone, or in combination with one or more other viruses (e.g., a second rAAV encoding having one or more different transgenes). In some embodiments, a compositions comprise 1, 2, 3, 4, 5, 6, 7, 8, 9, 10, or more different rAAV each having one or more different transgenes.

Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVS are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

An effective amount of an rAAV is an amount sufficient to target infect an animal, target a desired tissue, and produce a stable somatic transgenic animal model. The effective amount will depend primarily on factors such as the species, age, weight, health of the animal, and the tissue to be targeted, and may thus vary among animal and tissue. For example, a effective amount of the rAAV viral vector is generally in the range of from about 1 ml to about 100 ml of solution containing from about $10^9$ to $10^{16}$ genome copies. In some cases, a dosage between about $10^{11}$ to $10^{12}$ rAAV genome copies is appropriate. In certain preferred embodiments, $10^{12}$ rAAV genome copies is effective to target heart, liver, and pancreas tissues. In some cases, stable transgenic animals are produced by multiple doses of an rAAV.

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the AAV vector-based therapeutic constructs in suitably formulated pharmaceutical compositions disclosed herein either subcutaneously, intraopancreatically, parenterally, intravenously, intramuscularly, intrathecally, or even orally, intraperitoneally, or by nasal inhalation, including those modalities as described in U.S. Pat. Nos. 5,543,158; 5,641,515 and 5,399,363 (each specifically incorporated herein by reference in its entirety). One preferred mode of administration is by portal vein. Solutions of the active compounds as freebase or pharmacologically acceptable salts may be prepared in sterile water and may also suitably mixed with one or more surfactants, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active AAV vector in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The AAV vector compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present invention into suitable host cells. In particular, the rAAV vector delivered trangenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trails examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å containing an aqueous solution in the core.

Alternatively, nanocapsule formulations of the AAV vector-based polynucleotide may be used. Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV vector compositions to a host. Sonophoresis (ie., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

The agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

For instance a kit is provided for identifying an AAV serotype and/or for distinguishing novel AAV from known AAV. Other kits provided herein are for detecting the presence of a known or unknown AAV in a sample. Yet another kit of the invention involves the use of a sponge sequence for analyzing miRNA function.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

Kits are useful in some instances for rescuing contaminates by helper AAV infections and/or detection of latent virus that is transcriptionally active. Examples of such are shown in the examples.

The containers of the kit may house, for instance, any one or more of the following: at least one RNA detection component, at least one primer that has substantial homology with a nucleic acid sequence that is about 90% conserved between at least two AAV serotypes, at least one primer that is substantially complementary to a nucleic acid sequence corresponding to a 5' or 3' untranslated region of an AAV transcript such as a transcript encoding a rep and/or cap gene, a set of PCR primers specific for a signature region of the AAV nucleic acid sequence, a set of PCR primers specific for the full-length AAV capsid transcript (i.e., the p40 initiated transcript), two or more additional sets of primers, as described herein, and/or PCR probes, a primer having a sequence as set forth in SEQ ID NO: 1, SEQ ID NO: 2, SEQ ID NO: 3 or SEQ ID NO: 4.

The kits may also include reagents for Reverse transcription components that may include the following components: (a) at least one primer; (b) a Reverse Transcriptase (e.g., a Superscript); (c) nucleotides (e.g., dNTPs); and (d) RT buffer. In some embodiments, the at least one primer is complementary to a portion of an AAV cDNA sequence. In some embodiments, the at least one primer is an OligodT primer. In some embodiments, the kits further comprise reagents for PCR components that may include the following components: (a) at least one primer; (b) a thermostable polymerase (e.g., a Taq polymerase); (c) nucleotides (e.g., dNTPs); and (d) PCR buffer. In some embodiments, the at least one primer is complementary to a portion of an AAV cDNA sequence. In some embodiments, the kits comprise a DNA isolation kit (e.g., Oragene, OG-100) and/or an RNA isolation kit (e.g., oligodT-cellulose columns).

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the invention may include, instructions, a negative and/or positive control, containers, diluents and buffers for the sample, sample preparation tubes and a printed or electronic table of reference AAV sequence for sequence comparisons.

EXAMPLES

Example 1

Micro RNA Regulated Tissue Specific Transduction by rAAV Vector

Micro RNAs (miRNAs) are small RNA species with approximately 18-24 nucleotides in size. They regulate gene expression by post-transcriptional silencing through pairing to the partially complementary sites located in the 3' UTRs of transcripts of the target genes. Regulation of transgene expression in a cell type specific manner by endogenous miRNA was first introduced into lentiviral vectors to suppress transgene expression in hematopoietic cells and abolish transgene immunity. Many of the novel AAV vectors that were discovered recently demonstrate strong hepatic tissue tropism while exhibiting unique trandsduction profiles in other tissues. Depending on the applications, intended target tissue and gene of interest to be delivered, inadvertent transduction in liver and other tissues may lead to untoward outcomes which should be avoided. Previously, we have shown that systemic delivery of AAV9 vector can efficiently transduce liver, heart, pancreas, skeletal and diaphragm muscles with an expression cassette driven by an ubiquitous promoter such as chicken β-actin prompter (CB). We also demonstrated that tissue specific expressional targeting in myocardium and islet could be accomplished by introducing tissue/cell type specific promoter into the expression cassette, although levels of transgene expression in the target tissues were somewhat compromised and some off-target expression in liver was detected in the high dose regimen ($10^{12}$ GC/mouse).

In the present study, we explored use of endogenous miR-NAs to regulate tissue specific transduction profiles of rAAV in mouse models. In a proof-of-concept experiment, we tested the potency of miRNA mediated transgene silencing in mouse liver by introducing the binding sites of mi122, the most abundant micro RNA species in the liver, to the TBG promoter (the strongest liver specific promoter in our lab) driven nLacZ expression cassette. The rAAV vectors with and without mi122 binding sites were packaged with AAV9 capsid and delivered at high dose ($1 \times 10^{12}$ GC/mouse) to mouse liver via IV injections. X-gal histochemical staining of the liver sections at four weeks after gene transfer revealed almost complete suppression of nLacZ transduction in the liver of animals injected with the construct containing mi122 binding sites, suggesting endogenous mi122 RNA mediated transgene silencing in mouse liver is highly effective. The same vector design was then applied to the CbnLacZ construct for a similar comparison of expressional targeting for mouse liver, heart and some other tissues. The mi122 binding site bearing construct led to a 100% suppression of liver transduction without any impact on the heart and pancreas transduction. Other manipulations in endogenous microRNA mediated regulation of transgene expression have also been investigated. These include the dose response of gene silencing to the numbers of miRNA binding sites, simultaneous transgene suppression in multiple tissues and cell types through different miRNA species, and rescue of transgene expression from miRNA mediated gene silencing by miRNA sponge, etc.

Figure 1B:
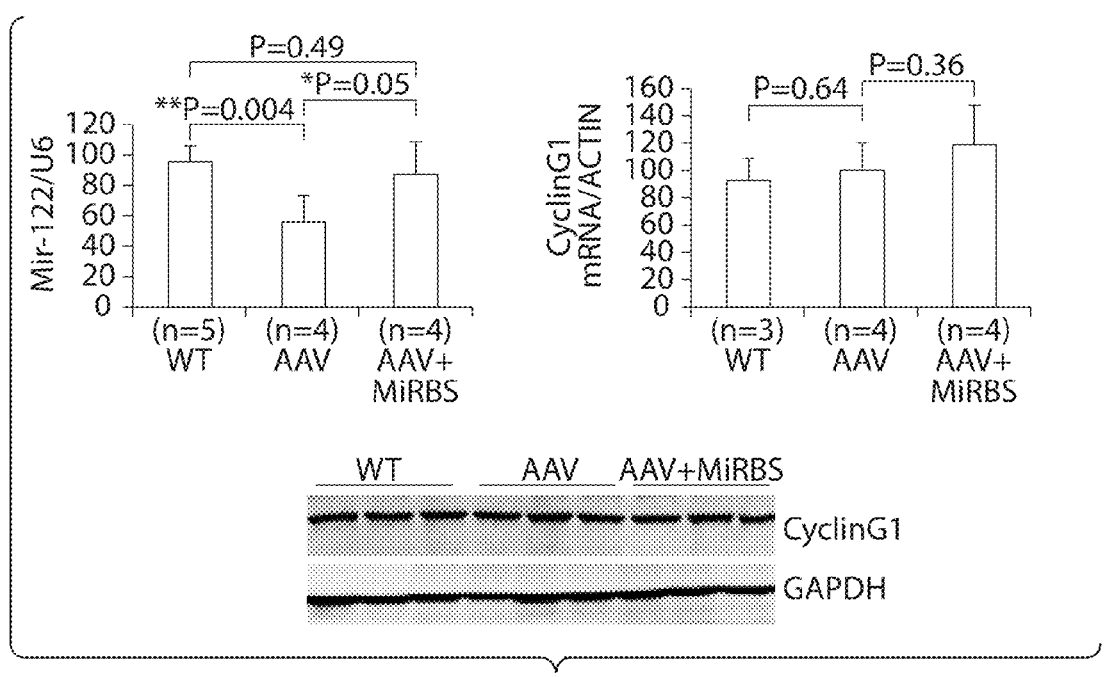
FIG. 1B shows that expression of AAV-miRBS, which contains binding sites for miR-122 does not significantly affect miR-122 expression compared with wild-type control, or mRNA or protein expression of the miR-122 target gene, Cyclin G1.
Figure 12:
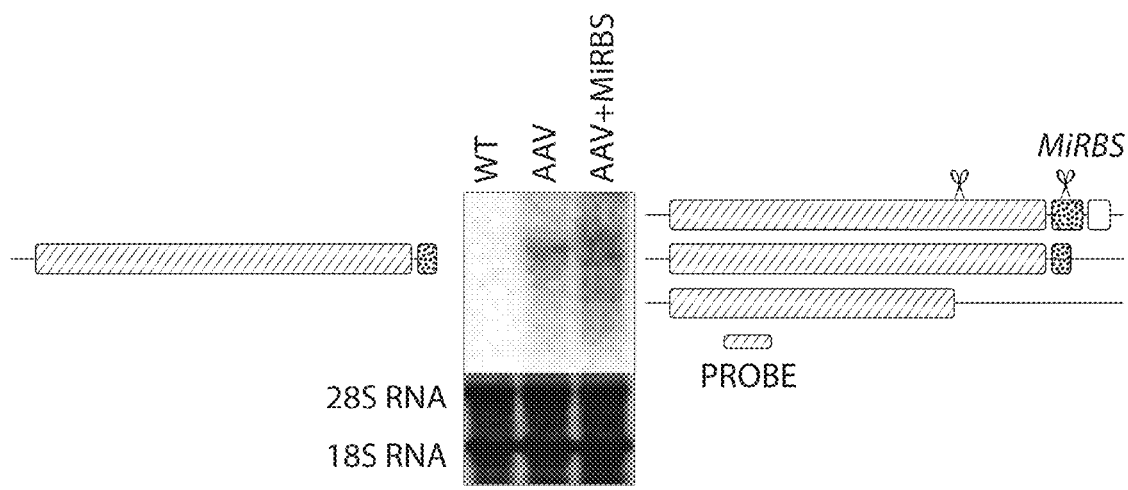
FIG. 12 depicts northern blot analysis of LacZ mRNA cleavage.

The ability of rAAVs to deliver transgenes that are susceptible to miRNA targeting and degradation was assessed. AAV-miRBS was constructed (FIGS. 11 and 12). AAV-miRBS is a transgene having a lacZ coding sequence, a miR-122 binding site and was determined to be susceptible to miR-122 based cleavage. (FIG. 1A). Expression of AAV-miRBS, which contained binding sites for miR-122 did not significantly affect miR-122 expression or Cyclin G1 expression (mRNA or protein), which is a target of miR-122. (FIG. 1B).

Figure 2A:
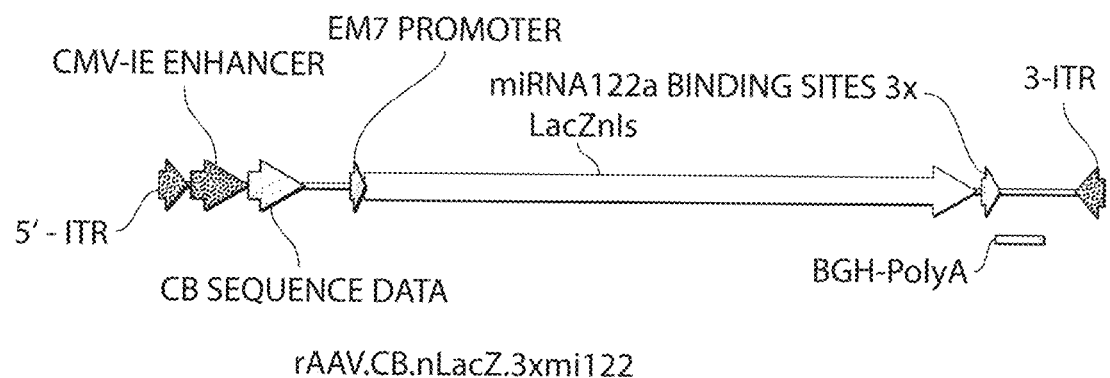
FIG. 2A is a schematic of a recombinant AAV, rAAV9.CB.nLacZ.3xmiR122, that contains a LacZ coding sequence flanked by 5' and 3' inverted terminal repeat sequences. rAAV.CB.nLacZ.3xmi122 also has a ubiquitous EM7 promoter, CMV immediate early enhancer and chicken beta-actin promoter sequences, and three miR-122 binding sites in the 3' UTR.
Figure 2B:
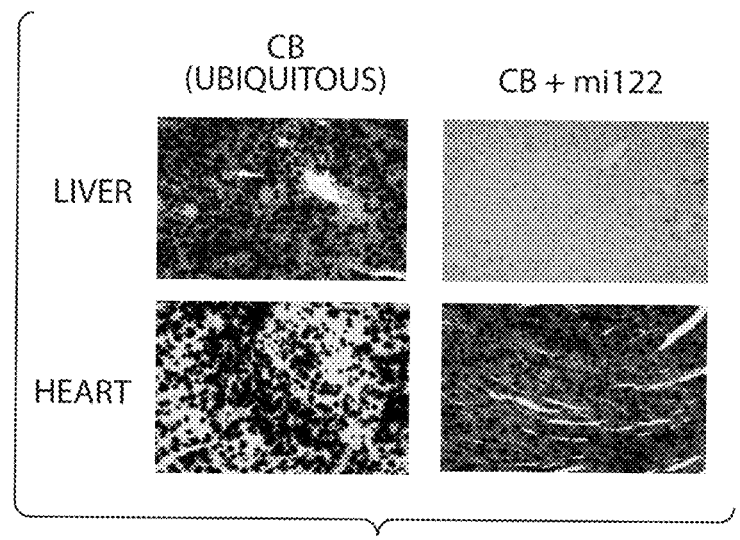
FIG. 2B shows that mice infected with rAAV.CB.nLacZ.3xmiR122 exhibit detectable LacZ expression (as detected by X-Gal staining) in heart tissue but not liver tissue, where miR-122 is expressed, whereas a control rAAV that does not contain miR122 binding sites is expressed in both heart and liver tissue.

A recombinant AAV, rAAV9.CB.nLacZ.3xmiR122, was constructed that contains a LacZ coding sequence flanked by 5' and 3' inverted terminal repeat sequences. rAAV.CB.nLacZ.3xmi122 also has a ubiquitous EM7 promoter, CMV immediate early enhancer and CB promoter sequences, and three miR-122 binding sites in the 3' UTR. (FIG. 2A.) Mice were infected with the rAAVs at high dose ($1 \times 10^{12}$ GC/mouse) and LacZ expression was evaluated in the heart and liver tissue. Expression of rAAV.CB.nLacZ.3xmiR122 is detectable by B-Galactosidase staining in heart tissue but not liver tissue, where miR-122 is expressed. (FIG. 2B.) Control rAAV that does not contain miR122 binding sites is expressed in both heart and liver tissue. (FIG. 2B.)

Figure 3:
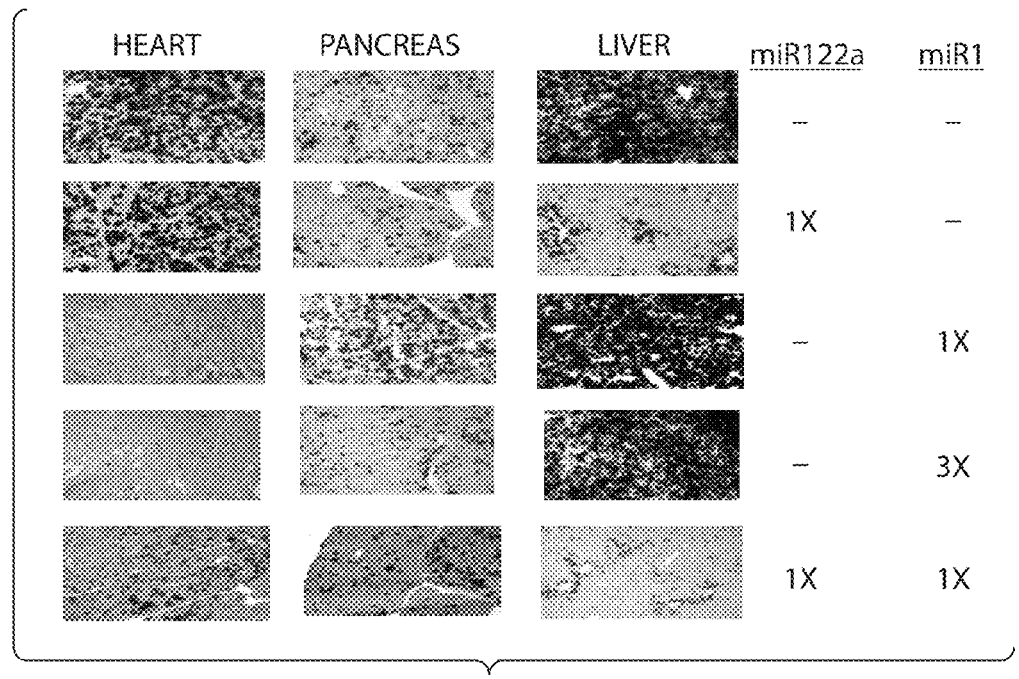
FIG. 3 depicts X-Gal staining of heart, pancreas and liver tissue sections from mice infected with recombinant AAVs that express a LacZ reporter gene controlled by a chicken beta actin promoter, each having miR-122 binding sites and/or miR-1 binding sites in its 3' UTR. Control rAAVs, which express a LacZ reporter gene controlled by a chicken beta actin promoter without miRNA binding sites, produced high levels of LacZ expression in heart and liver tissue. (first row.) rAAVs with a single miR-122 site in the 3'-UTR produced high levels of LacZ reporter gene expression in heart tissue but not pancreas or liver tissue. (second row.) rAAVs with a single (or three) miR-1 site(s) in the 3'-UTR produced high levels of LacZ reporter gene expression in liver tissue but not pancreas or heart tissue. (third and fourth rows.) rAAVs with a single miR-1 site and a single miR-122 site in the 3'-UTR did not produce significant levels of LacZ reporter gene expression in any of the three tissues. (fifth row.)

Recombinant AAVs were produced that express a LacZ reporter gene controlled by a chicken beta actin promoter, each having miR-122 binding sites and/or miR-1 binding sites in its 3' UTR. Control rAAVs were also produced that express a LacZ reporter gene controlled by a chicken beta actin promoter without miRNA binding sites. Mice were infected with the rAAVs at high dose ($1 \times 10^{12}$ GC/mouse) and LacZ expression was evaluated by X-Gal staining of heart, pancreas and liver tissue sections. Control rAAVs produced high levels of LacZ expression in heart and liver tissue. (FIG. 3, first row.) rAAVs with a single miR-122 site in the 3'-UTR produced high levels of LacZ reporter gene expression in heart tissue but not pancreas or liver tissue, indicating that endogenous miR-122 inhibited LacZ expression in the liver. (FIG. 3, second row.) rAAVs with a single (or three) miR-1 site(s) in the 3'-UTR produced high levels of LacZ reporter gene expression in liver tissue but not pancreas or heart tissue, indicating that endogenous miR-1 inhibited LacZ expression in the heart. (FIG. 3, third and fourth rows.) rAAVs with a single miR-1 site and a single miR-122 site in the 3'-UTR did not produce significant levels of LacZ reporter gene expression in any of the three tissues. (FIG. 3, fifth row.) This result indicates that endogenous miR-1 inhibited LacZ expression in the heart, that endogenous miR-122 inhibited LacZ expression in the heart, and that multiple different miRNA binding sites can be combined to inhibit expression in multiple different tissues.

Example 2 rAAV Mediated Delivery of Target Specific Micro RNA Sponges for Study of Micro-RNA Function in Mouse Models Micro RNAs (miRNAs) are approximately 18-24 nucleotide long small RNA species. They regulate most of cellular processes including differentiation, apoptosis, proliferation and maintain cell and tissue identify. These functions are accomplished by post-transcriptional silencing by pairing to the partially complementary sites located in the 3' UTRs of transcripts of the target genes. Changes in miRNA expression profiles could be implicated in human diseases. It has been predicted that at least a thousand of miRNA species exist in human. However, biological functions of the majority of miRNAs in mammals are poorly understood. One of the approaches to study miRNA functions is to knock down their expression and examine resulting biological consequences. The strategies for miRNA knock-down include miRNA sponge, target masking and erase, which modifies miRNA expression profiles by either scavenging miRNA or blocking miRNA binding to the target sequences. These have proven to be effective in primarily in vitro studies. Use of those designs to study miRNA functions in vivo has been hindered by lack of efficient delivery tools for sustained alternation of miRNA profiles.

Adeno-associated virus (AAV) is a small and non-pathogenic, single stranded DNA virus. Recent advancement in (AAV) vectorology has generated a battery of novel AAV serotype vectors that are capable of achieving efficient and stable gene transfer to major target tissues, which makes rAAV an ideal tool for in vivo gene transfer. In an attempt to investigate miRNA functions in vivo, we utilized rAAV platform for efficiently delivering target specific miRNA sponges to mouse models. In a proof-of-concept study, we selected miR-122 and Let-7 as the targets. MiR-122 is the most abundant miRNA in liver and plays important roles in regulating lipid metabolism. Let-7 is highly expressed in early development and tumor cells. It has been implicated in transformation and tumorigenesis. We incorporate bulged binding sites for those two miRNA species into the 3' UTR of the fire fly luciferase for packaging with AAV9 capsid. Transcription of luciferase gene and bulged miRNA binding sequences is directed by either chicken-β-actin promoter or liver specific promoter TBG. The vector genomes also carries a GFP reporter gene cassette that is not regulated by miRNA to serve as a microscopic tracer for gene transfer. Vector constructs with wild type and mutant miRNA sponges are delivered to mice for side by side comparison. The animals are monitored for luciferase expression alive to document translational suppression by wild type miRNA sponges. Lipid profiles of the animals received mi122 sponges are scrutinized. Serum levels of α-fetal proteins, tumor incidence and other gross pathology are documented in the animals injected with Let-7 sponges. In addition, animals are sacrificed at different time points. Total miRNA profiles and expression level of dicer RNA are analyzed in the target tissues.

MicroRNA sponges are competitive inhibitors of microRNAs. MicroRNA sponge transcripts may contain multiple, tandem binding sites to a microRNA of interest. In some cases, sponges can derepress microRNA targets at least as strongly as chemically modified antisense oligonucleotides against microRNAs. Sponges specifically inhibit microRNAs with a complementary heptameric seed, such that a single sponge can be used to block an entire microRNA seed family. Sponges may be expressed from a RNA polymerase II promoter (Pol II)-driven and may be combined with a reporter gene (e.g., luciferase, EGFP, etc.) for identification and sorting of sponge-treated cells. (See, e.g., Ebert M S, Neilson J R, Sharp P A. *Nature Methods*. 2007, 4(9):721-726.) The skilled artisan will appreciate that the design of miRNA expression constructs involves an assessment of various factors including promoter selection, e.g., a Polymerase III promoter, e.g., a U6 promoter, versus Polymerase II promoter, binding site design, e.g., perfect match versus bulge, and seed sequence selection, e.g., a sponge with an appropriately designed seed sequence may universally knock-down an entire miRNA seed family. For example, binding sites for a particular microRNA seed family (miR-21) were perfectly complementary in the seed region with a bulge at positions 9-12 to prevent RNA interference-type cleavage and degradation of the sponge RNA by Argonaute 2. (Ebert M S, Neilson J R, Sharp P A. *Nature Methods*. 2007, 4(9):721-726.) Exemplary seed families include let-7, which has a seed sequence of 5'-GAGGUAG-3' and comprises Let-7, miR-84, miR-241, and miR-48), and miR30, which has a seed sequence of 5'-GUAAACA-3' and comprises miR30a and miR30e.

Let-7 Sponges

Let-7 represses both the mRNA and proteins levels encoded by Dicer and HMGA2. This repression is not caused by direct cleavage of these two target genes; but it may infect the steady-state levels of the target mRNAs by a mechanism distinct from Argonaute2-catalyzed endonucleolytic cleavage. Because Let-7 regulates expression of the microRNA Processing Enzyme, Dicer, it provides a model for studying feedback control by the human microRNA.

Figure 4:
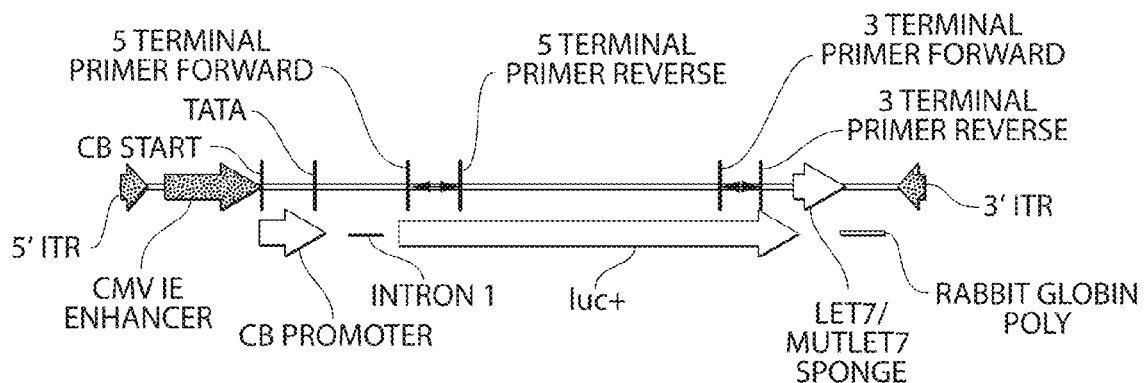
FIG. 4 depicts rAAV-9-based Let-7 sponge delivery vector having 5'- and 3'-inverted terminal repeat regions, a CMV immediate early enhancer, a chicken beta-actin promoter, a luciferase reporter gene, one or more sponge sequences, and a globin poly-A tail sequence.
Figure 5A:
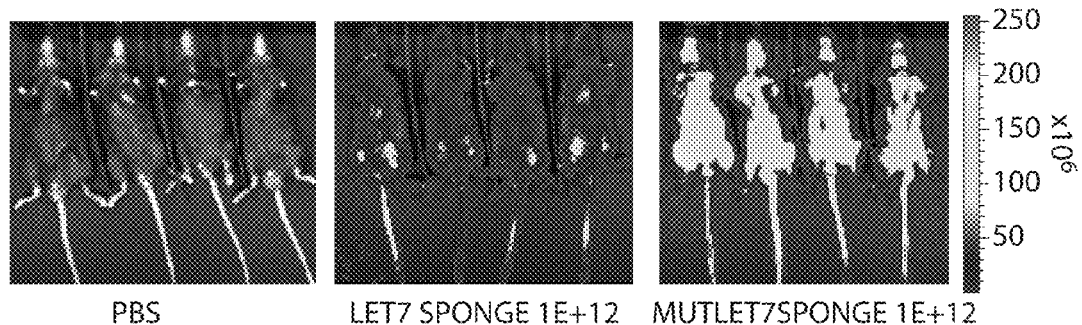
FIG. 5A depicts live luciferase imaging of mice four weeks after IV administration of either rAAV9CB.FFLuc.7XLet7 sponge or rAAV9CB.FFLuc.7X Let7-mutant sponge.
Figure 5B:
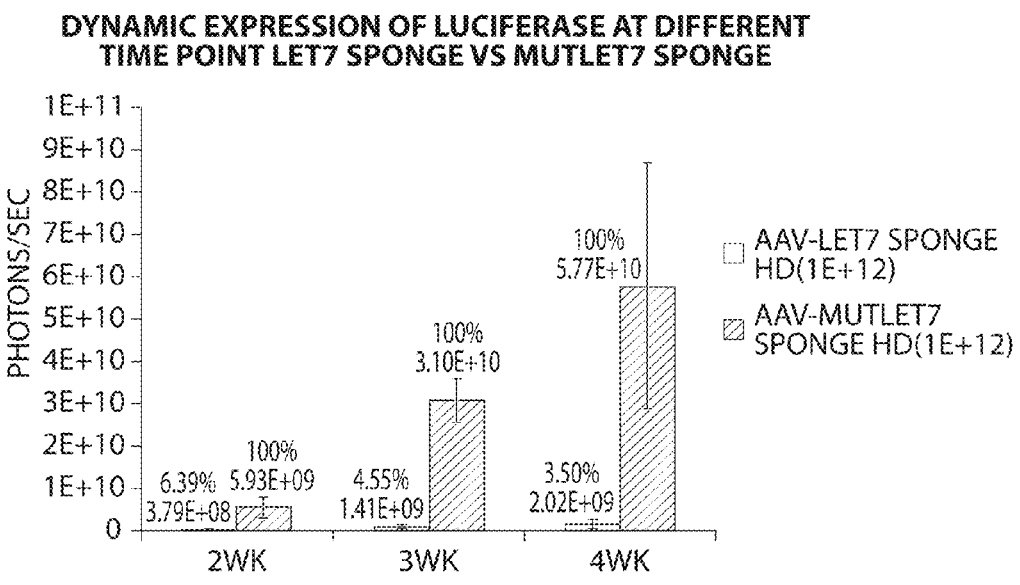
FIG. 5B shows that luciferase expression (photons/sec) was persistent up to four weeks post injection.
Figure 6A:
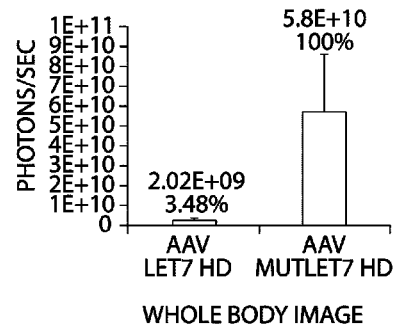
FIG. 6A shows a comparison of luciferase radiance (photons/sec) between let-7 and mutant let-7 treated mice at the same injection dose from whole body imaging.
Figure 6B:
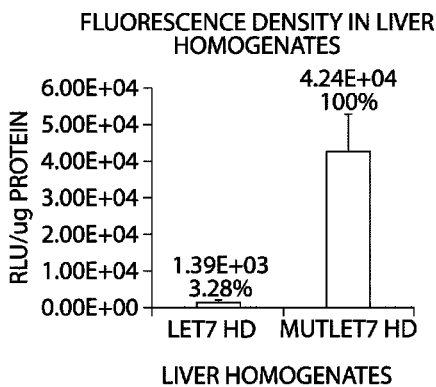
FIG. 6B shows a comparison of luciferase fluorescence density (RLU/ug protein) between let-7 and mutant let-7 treated mice at the same injection dose from liver homogenates.
Figure 6C:
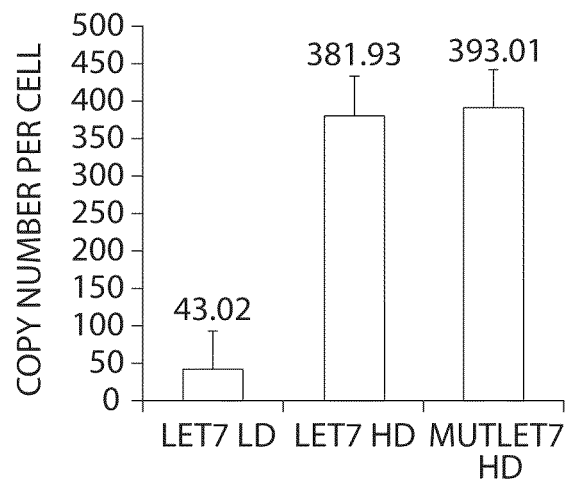
FIG. 6C shows that transgene copy numbers per cell in animal livers were dependent on injection dose (low dose (LD), 1E11 genomic copies/mouse or high dose (HD), 1E12 genomic copies/mouse).

A rAAV-9-based Let-7 sponge delivery vector was constructed, which comprised 5'- and 3'-inverted terminal repeat regions, a CMV immediate early enhancer, a chicken beta-actin promoter, a luciferase reporter gene, one or more sponge sequences (against let-7), and a globin poly-A tail sequence. As a control, an identical vector was a constructed having a mut-Let-7 sponge sequence. (FIG. 4, showing rAAV9CB.FFLuc.7XLet7 sponge and rAAV9CB.FFLuc.7X Let7-mutant sponge.) Let7 sponge sequences are shown in FIG. 14. Mice were injected with $10^{12}$ genomic copies of rAAV-9 sponge delivery vector by IV administration. Four weeks after injection luciferase activity was evaluated in the live mice by luciferase imaging. Mice infected with both rAAV9CB.FFLuc.7XLet7 sponge and rAAV9CB.FFLuc.7X Let7-mutant sponge exhibited luciferase activity throughout. (FIG. 5A.) Luciferase expression was persistent up to four weeks post infection. (FIG. 5B.) Luciferase expression was consistently higher in the rAAV9CB.FFLuc.7X Let7-mutant sponge infected mice compared with rAAV9CB.FFLuc.7XLet7 sponge infected mice, at the same dose. (FIGS. 6A and B). Copy numbers of let7 and mutant-let7 transgenes in cells of the liver were essentially the same between the two groups, at the same dose. (FIG. 6C.) This result is consistent with miR-122 binding specifically to rAAV9CB.FFLuc.7X Let-7 sponge (and not rAAV9CB.FFLuc.7X Let-7-mutant sponge) and inhibiting luciferase protein expression.

miR122 Sponges

MiR-122, which is primarily expressed in the liver, inhibits expression of Cyclin G1, Bcl-w, Cat1 and other genes, promotes HCV replication and regulates lipid and cholesterol metabolism. Elmen et al. have shown that LNA-antimiR-122 reduces total plasma cholesterol levels in a dose dependent manner (See, e.g., FIGS. 1 and 2 of Elmen J, et al. Nature, 2008, 452: 896-900.)

Figure 8:
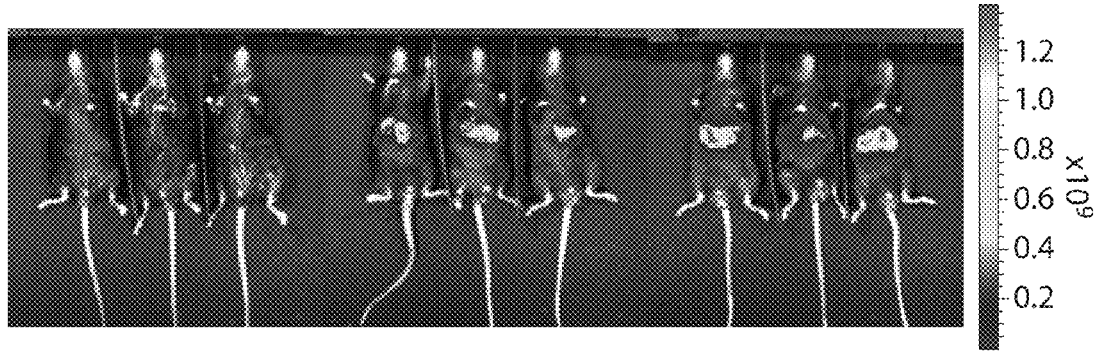
FIG. 8 depicts live luciferase imaging of C57BL/6 mice three weeks after IV administration of either rAAV9TBG.FFLuc.7X miR-122 sponge or rAAV9 rAAV9TBG.FFLuc.7xmiR-122-mutant sponge. In both cases luciferase activity was detected mainly in the abdomen.
Figure 9:
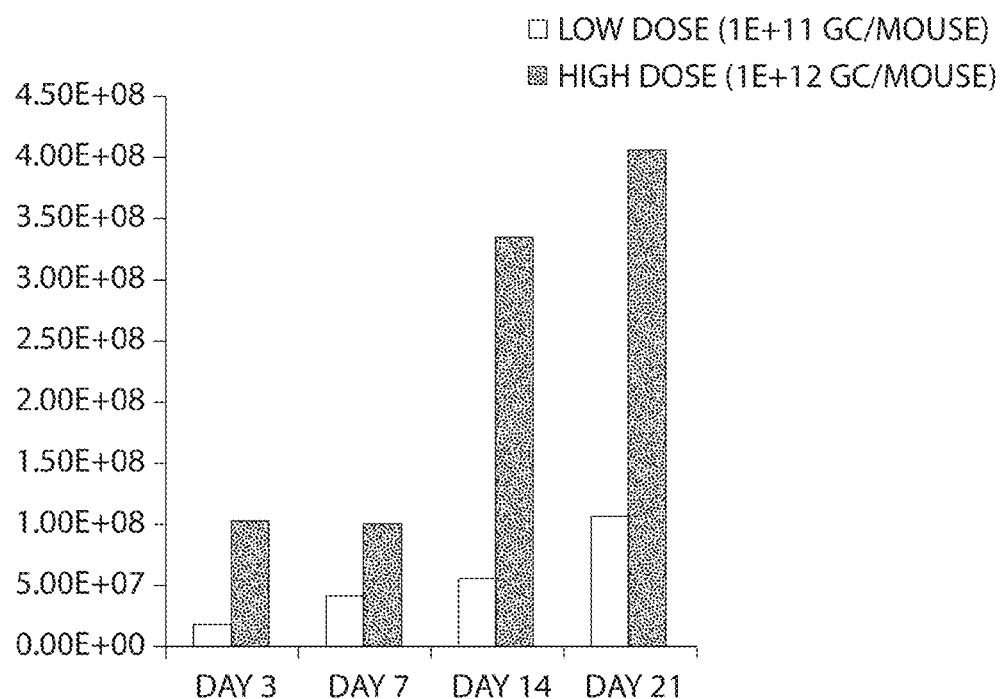
FIG. 9 depicts a bar graph of a comparison of luciferase expression, at multiple time points, between mice injected with a low dose (1E11 genomic copies/mouse) or a high dose (1E12 genomic copies/mouse) of rAAV9CB.FFLuc.7xmiR-122 sponge.
Figure 10A:
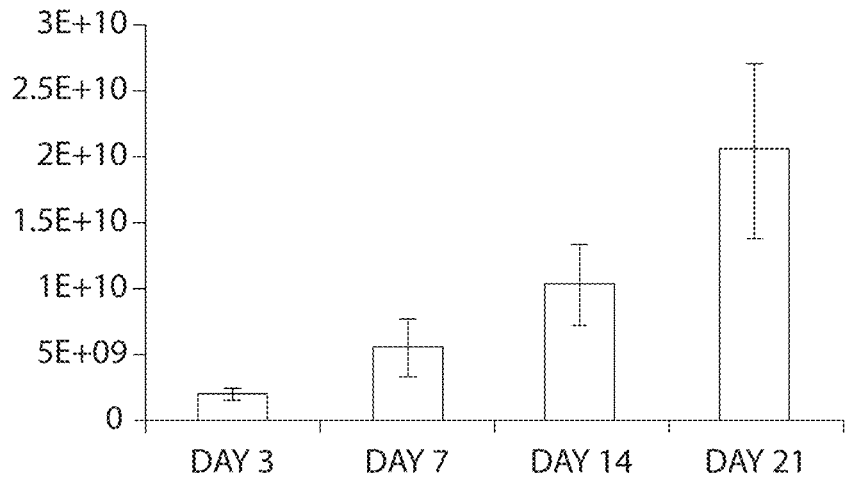
FIG. 10A depicts a bar graph of luciferase expression at multiple time points in mice injected with rAAV9CB.FFLuc.7xmiR-122-mutant sponge (1E12 genomic copies/mouse).
Figure 10B:
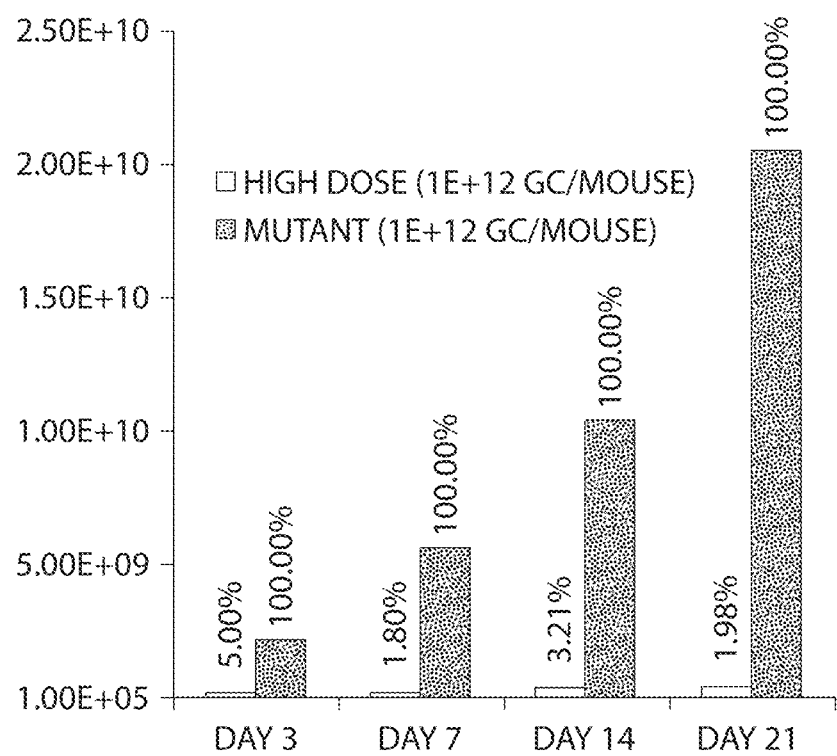
FIG. 10B depicts a bar graph of a comparison of luciferase expression, at multiple time points, between mice injected with rAAV9CB.FFLuc.7xmiR-122 sponge or rAAV9CB.FFLuc.7xmiR-122-mutant sponge (1E12 genomic copies/mouse).
Figure 11A:
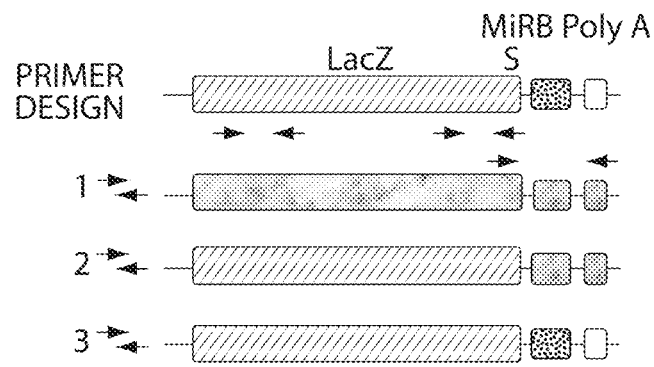
FIG. 11A depicts three primer set locations for amplifying LacZ mRNAs.
Figure 11B:
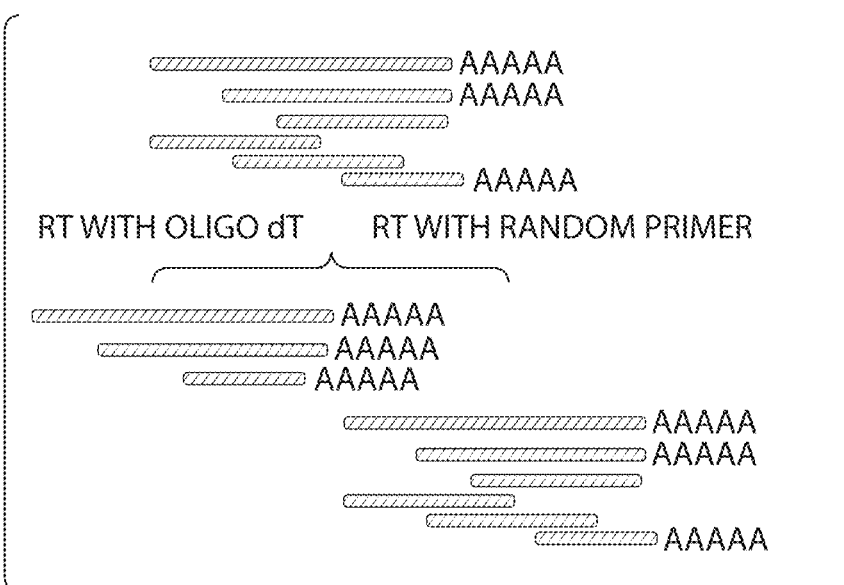
FIG. 11B depicts hypothetical RT-PCR results with both oligo dT and random primer RT steps.
Figure 11C:
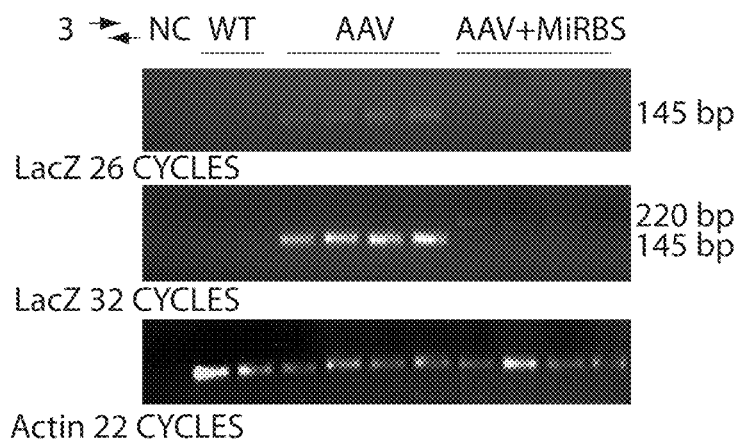
FIG. 11C depicts RT-PCR results using primer set 3 of FIG. 11A.
Figure 11D:
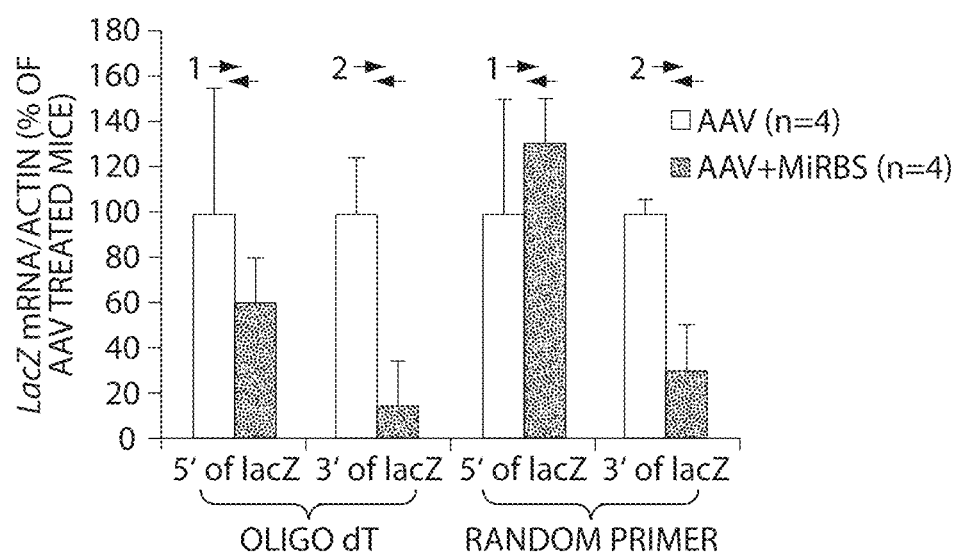
FIG. 11D depicts RT-PCR results using primer sets 1 and 2, with oligo dT or random priming RT steps. For FIGS. 11C and 11D, RNA was obtained from mice expressing LacZ without miRNA binding sites (AAV) or with miRNA binding sites (AAV+miRBS).
Figure 13:
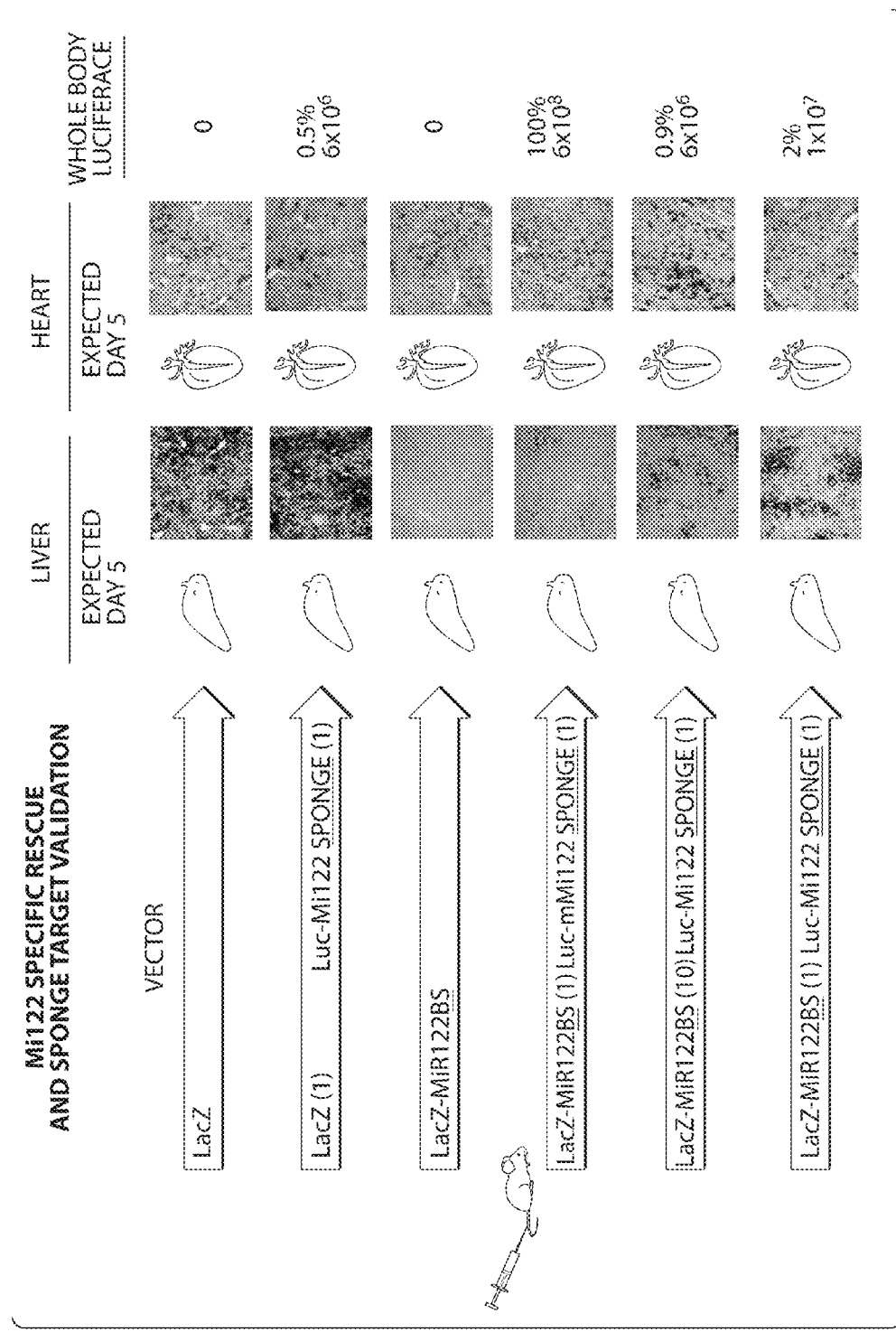
FIG. 13 depicts MiR-122 specific rescue and sponge target validation.

A rAAV-9-based miR-122 sponge delivery vector was constructed, which comprised 5'- and 3'-inverted terminal repeat regions, a CMV immediate early enhancer, a chicken beta-actin promoter, a luciferase reporter gene, one or more sponge sequences (against miR-122), and a globin poly-A tail sequence. As a control, an identical vector was a constructed having a mutant miR-122 sponge sequence. FIG. 7 shows the structure of miR122 sponge sequences. C57BL/6 mice were injected with $10^{11}$ or $10^{12}$ genomic copies of the rAAV-9 sponge delivery vectors by IV administration. Three weeks after injection luciferase activity was evaluated in the live mice by luciferase imaging. Mice infected with either rAAV9TBG.FFLuc.7xmiR-122 sponge or rAAV9TBG.FFLuc.7xmiR-122-mutant sponge exhibited luciferase activity mainly in the abdomen. (FIG. 8.) Luciferase expression was dependent on treatment dose and increased in a time-dependent manner, as observed up to three weeks post infection. (FIGS. 9 and 10A.) Luciferase expression was consistently higher in the rAAV9TBG.FFLuc.7xmiR-122-mutant sponge infected mice. (FIG. 10B.) This result is consistent with miR-122 binding specifically to rAAV9TBG.FFLuc.7xmiR-122 sponge (and not rAAV9TBG.FFLuc.7xmiR-122-mutant sponge) and inhibiting luciferase protein expression. FIG. 13 depicts an miR122 specific rescue experiment. Mice are infected with LacZ having miR122 binding sites. Expression in the liver is inhibited by endogenous miR122, and inhibition by endogenous miR122 is attenuated when mice are co-infected with miR122 sponge.

This invention is not limited in its application to the details of construction and the arrangement of components set forth in this description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A kit for producing a recombinant Adeno-Associated Virus (rAAV) that generates a somatic transgenic animal that expresses a transgene in a target tissue, the kit comprising:
at least one container housing a recombinant AAV vector, wherein the recombinant AAV vector comprises a transgene that expresses an RNA transcript that comprises at least one binding site for an miRNA that is expressed in cells of an off-target tissue of the animal, wherein, when the miRNA and the RNA transcript are present together in cells of the off-target tissue, the miRNA hybridizes to the at least one binding site of the RNA transcript and inhibits activigty of the RNA transcript wherein the miRNA is miR-122 and the off-target tissue is liver;

at least one container housing a rAAV packaging component, wherein the packing componenet comprisies a host cell comprising at least one cap gene encoding a capsid protein of AAV9; and instructions for constructing and packaging the rAAV, wherein the rAAV transduces cells of the target tissue.

2. The kit of claim 1, wherein the host cell further comprises at least one rep gene.

3. The kit of claim 1, wherein the RNA transcript is an exogenous miRNA.

4. The kit of claim 1, wherein the transcript is an mRNA transcript that encodes a protein.

5. The kit of claim 1, wherein the transgene comprises a tissue specific promoter or inducible promoter operatively linked to a coding region from which the RNA transcript is expressed.

6. the kit of claim 1, wherein the rAAV has an Inverted Terminal Repeat (ITR) sequence from an AAV serotype selected from: AAV1, AAV2, AAV3AAV4, AAV5, AAV6, AAV7, AAV8, AAV9, AAV10, AAV11, and AAV12, and variants thereof.

7. The kit of claim 1, wherein the product of the transgene causes a pathological state in the animal.

8. The kit of claim 1, wherein the product of the transgene is a reporter molecule.

9. A recombinant adeno-associated virus (rAAV) comprising:
an AAV9 in which is packaged a transgene that encodes an RNA transcript that comprises at least one binding site for miR-122 that inhibits expression of the RNA transcript in liver.

10. The rAAV of claim 9. wherein the transgene comprises up to three binding sites for miR-122.

11. The rAAV of claim 9. wherein the RNA transcript is an exogenous miRNA.

12. The rAAV of claim 9, wherein the transcript is an mRNA transcript that encodes a protein.

13. The rAAV of claim 1, wherein the rAAV has an Inverted Terminal Repeat (ITR) sequence from an AAV serotype selected from : AAV1, AAV2, AAV3,AAV4, AAV5, AAV6, AAV7, AAV8, AAV9, AAV10, AAV11, and AAV12, and variants therof.

14. The rAAV of claim 9, wherein the transgene comprises a tissue specific promoter operatively linked to a coding region from which the RNA transcript is expressed.

* * * * *